United States Patent
Camilleri et al.

(10) Patent No.: US 11,248,093 B2
(45) Date of Patent: Feb. 15, 2022

(54) INVERSE EMULSION THICKENERS

(71) Applicant: Scott Bader Company Ltd., Northamptonshire (GB)

(72) Inventors: Lee Camilleri, Buckinghamshire (GB); Clive Noel Williams, Northamptonshire (GB); Paul Edward Hunt, Buckinghamshire (GB)

(73) Assignee: Scott Bader Company LTD., Northamptonshire (GB)

( * ) Notice: Subject to any disclaimer, the term of this patent is extended or adjusted under 35 U.S.C. 154(b) by 7 days.

(21) Appl. No.: 16/652,469

(22) PCT Filed: Oct. 4, 2018

(86) PCT No.: PCT/EP2018/077050
§ 371 (c)(1),
(2) Date: Mar. 31, 2020

(87) PCT Pub. No.: WO2019/068830
PCT Pub. Date: Apr. 11, 2019

(65) Prior Publication Data
US 2020/0231762 A1    Jul. 23, 2020

(30) Foreign Application Priority Data

Oct. 5, 2017 (GB) .................................. 1716314

(51) Int. Cl.
| | |
|---|---|
| *A61K 8/06* | (2006.01) |
| *A61K 8/31* | (2006.01) |
| *A61K 8/81* | (2006.01) |
| *C08J 3/09* | (2006.01) |
| *A61Q 1/00* | (2006.01) |
| *A61Q 17/04* | (2006.01) |
| *A61Q 19/00* | (2006.01) |

(52) U.S. Cl.
CPC .............. *C08J 3/092* (2013.01); *A61K 8/064* (2013.01); *A61K 8/31* (2013.01); *A61K 8/8158* (2013.01); *A61Q 1/00* (2013.01); *A61Q 17/04* (2013.01); *A61Q 19/00* (2013.01); *A61Q 19/002* (2013.01); *A61K 2800/48* (2013.01); *C08J 2333/26* (2013.01)

(58) Field of Classification Search
None
See application file for complete search history.

(56) References Cited

U.S. PATENT DOCUMENTS

| | | |
|---|---|---|
| 3,284,393 A | 11/1966 | Vanderhoff et al. |
| 3,826,771 A | 7/1974 | Anderson et al. |
| 4,077,930 A | 3/1978 | Lim et al. |
| 4,626,363 A | 12/1986 | Gleason et al. |
| 7,015,279 B2 | 3/2006 | Braun et al. |
| 7,956,012 B2 | 6/2011 | Gupta et al. |
| 8,419,976 B2 | 4/2013 | Song et al. |
| 2001/0051686 A1 | 12/2001 | Tabacchi et al. |
| 2001/0053801 A1 | 12/2001 | Tabacchi et al. |
| 2002/0032243 A1 | 3/2002 | Tabacchi et al. |
| 2006/0269490 A1 | 11/2006 | Braun et al. |
| 2008/0051492 A1 | 2/2008 | Mitarotonda et al. |
| 2011/0076245 A1 | 3/2011 | Braun et al. |
| 2013/0236401 A1 | 9/2013 | Mallo et al. |
| 2014/0221258 A1* | 8/2014 | Ohler .................. C10M 105/02 508/110 |
| 2015/0025193 A1 | 1/2015 | Doolan et al. |

(Continued)

FOREIGN PATENT DOCUMENTS

| | | |
|---|---|---|
| EP | 0186361 | 7/1986 |
| EP | 0503853 | 9/1992 |
| EP | 2215133 | 8/2010 |

(Continued)

OTHER PUBLICATIONS

International Search Report and Written Opinion for PCT/EP2018/077050 dated Dec. 11, 2018, 9 pages.

*Primary Examiner* — Jennifer A Berrios
(74) *Attorney, Agent, or Firm* — Adsero IP

(57) ABSTRACT

An inverse emulsion copolymer composition comprises (A) an aqueous phase comprising a cross-linked hydrophilic polyelectrolyte copolymer (A') obtained by the free radical copolymerisation of: (i) at least one anionic ethylenically unsaturated monomer bearing a negatively charged group and one polymerisable C=C double bond, or at least one cationic ethylenically unsaturated monomer bearing a positively charged group and one polymerisable C=C double bond, and (ii) at least one non-ionic ethylenically unsaturated cross-linking monomer bearing at least two polymerisable C=C double bonds, and (iii) optionally, one or more hydrophilic non-ionic ethylenically unsaturated monomers bearing one polymerisable C=C double bond, (B) an oil phase comprising a carrier oil (C), (D) (i) at least one water-in-oil emulsifying surfactant, and (D) (ii) at least one oil-in-water emulsifying surfactant; characterised in that the carrier oil component (C) of the oil phase comprises from 75% to 100%, by weight of the said carrier oil component (C), of farnesane (2, 6, 10-trimethyldodecane). The compositions are effective for use as thickeners for thickening aqueous solutions, including solutions which contain dissolved salts. The compositions also show excellent thickening in acidic solutions than counterpart compositions containing paraffinic oils.

20 Claims, No Drawings

(56) References Cited

U.S. PATENT DOCUMENTS

2015/0315520 A1   11/2015   Eppler et al.

FOREIGN PATENT DOCUMENTS

| FR | 2773805 | 7/1999 |
| FR | 2774688 | 8/1999 |
| FR | 2782086 | 2/2000 |
| WO | WO 00/32639 | 6/2000 |
| WO | WO 2017/059136 | 4/2017 |

* cited by examiner

INVERSE EMULSION THICKENERS

RELATED APPLICATIONS

This application is a 35 U.S.C. § 371 national stage application of PCT/EP2018/077050 (WO2019/068830 A1), filed on Oct. 4, 2018, which claims priority of United Kingdom patent application number 1716314.8, filed Oct. 5, 2017, the contents of each of which are incorporated herein by reference in their entireties.

Inverse emulsion copolymer thickeners have been known for several decades, with variations of the technology being described in numerous patent applications over that period. In essence, one or more water soluble ethylenically unsaturated polymerisable monomers are dissolved in aqueous solution, this aqueous solution then being emulsified into a carrier oil with the aid of one or more surfactants having HLB values low enough to generate a stable water-in-oil emulsion. Polymerisation is then triggered by means of a free radical initiator, resulting in a dispersion within the carrier oil of water droplets containing hydrophilic copolymer. Finally, a different surfactant, one of higher HLB value and capable of promoting oil-in-water emulsification, is added to the dispersion to give the inverse emulsion copolymer thickener. When this is added to a quantity of water or aqueous medium, the higher HLB surfactant causes the water-in-oil emulsion (the inverse emulsion) to invert, such that the aqueous phase becomes the continuous phase, releasing the copolymer dispersed within the said continuous phase into the quantity of water or aqueous medium that now mingles with the said continuous phase. The copolymer will then thicken this quantity of water or aqueous medium to which the inverse emulsion copolymer thickener has been added.

It is typically the case that at least one of the water soluble ethylenically unsaturated monomers used to form the copolymer is ionic in nature, usually being anionic in nature. Acrylic or methacrylic acids (hereinafter referred to as (meth)acrylic acid, as is common practice with such acids or their esters, denoting that either or a mixture of both may be equally useful), which may be partially or fully neutralised with an alkali such as sodium hydroxide or ammonium hydroxide, have found use as the anionic monomer. Another anionic monomer that has been widely used is 2-acrylamido-2-methyl-1-propane sulfonic acid (sometimes also termed 2-methyl-2[(1-oxo-2-propenyl)amino]-1-propane sulfonic acid, often also abbreviated to the acronym AMPS), which may also be partially or fully neutralised with alkali. The anionic monomer(s) may be copolymerised with one or more nonionic monomers, acrylamide being a particularly preferred non-ionic monomer within the art. Small quantities of monomer(s) bearing more than one site of ethylenic unsaturation are sometimes also included, imparting some degree of cross-linking to the copolymer. Methylene-bis-acrylamide (MBA) is often employed when such cross-linking is desired, though other cross-linkers such as triallylamine have also been used.

The carrier oil used within these inverse emulsion polymerisations is usually an aliphatic hydrocarbon oil supplied from within the petroleum industry. Isoparaffinic oils such as Isopar M, Isopar G, Marcol 52 and isohexadecane have been frequently employed.

Amongst the many patents describing anionic inverse emulsion copolymer thickeners according to the above general teaching may be listed French patent applications FR2773805, FR2774688 and FR2782086, European patent applications EP0186361 and EP0503853, and International (PCT) patent publication WO 00/32639. The examples in all of these documents all employ petroleum-derived oils of the abovementioned type as the carrier oils in their described inverse emulsion copolymers.

For example, EP0186361 discloses an anionic polymer derived from acrylic acid, AMPS, 2-sulphoethyl methacrylate and methylene-bis-acrylamide monomers, provided in an aqueous ammonia solution A, which is subsequently dispersed in an organic solvent medium B, mainly composed of an isoparaffinic oil, Isopar M ($C_{13}$ to $C_{14}$ isoparaffin).

US2006/0269490 shows various example anionic copolymer thickeners in isohexadecane. Examples 1 to 5 each illustrate an inverse latex of (AMPS Na salt)/dimethylacrylamide anionic copolymer, crosslinked with MBA, in an oil phase containing isohexadecane. According to [0026], the oil phase comprises a commercial mineral oil containing saturated hydrocarbons, for instance paraffins, isoparaffins or cycloparaffins. Squalane of plant origin is also mentioned.

US2008/0051492 discloses inverse emulsion copolymers prepared from a combination of anionic and cationic monomers. Examples 1 to 3 each show a copolymer prepared from AMPS Na salt, acrylic acid and acryloyloxyethyl trimethyl ammonium chloride, crosslinked with MBA. The copolymers are mixed with an oil phase containing either a $C_{13}$ to $C_{20}$ isoparaffin, a $C_{16}$ isoparaffin or a $C_{20}$ hydrogenated polydecene. According to [0038], amongst the saturated hydrocarbons proposed for the oil phase, $C_{13}$ to $C_{16}$ isoparaffin is the most preferred.

US 2013/0236401 shows in its preparation Example 1, an inverse latex of (AMPS Na salt)/acrylamide copolymer, crosslinked with MBA, which is mixed with an oil phase containing Isopar M. Further examples of saturated hydrocarbons, for instance paraffins, isoparaffins or cycloparaffins, including isohexadecane are disclosed at [0030]. Squalane is also mentioned as the example of a plant oil.

In recent years, however, the need has developed—driven by the recognition that petroleum-based feedstocks have a finite lifetime—to replace the petroleum-derived oils traditionally used within the art with oils derived from more renewable resources, such as oils derived from the fermentation of natural products.

US 2015/0315520 proposes compositions containing partially hydrogenated farnesene, wherein one, two or three of the double bonds are hydrogenated for use in cleaning and degreasing compositions. According to [0131], these unsaturated materials are expected to be useful as co-monomers in resins and elastomer formulations and as co-monomers in Friedel Crafts and radical polymerizations, owing to the presence of one or more double bonds. In view of their ability to participate in polymerization reactions these unsaturated materials are not appropriate for use as carrier oils for inverse emulsion copolymer thickeners.

It is generally believed by those skilled in the art that, when the ionic copolymer is released into an aqueous medium, the ionically charged groups repel each other electrostatically, causing the copolymer structure to extend or swell and thus increasing the viscosity of the aqueous medium. If, however, the aqueous medium contains dissolved salts, its dielectric constant is increased and consequently there is less repulsion between the ionic groups on the copolymer. Extension or swelling is consequently reduced, as is the thickening capability of the copolymer. It is not unusual to find that an inverse emulsion copolymer displaying good thickening activity in pure water proves to be inadequate when employed to thicken aqueous solutions containing dissolved salts.

This reduction in electrostatic repulsion is also believed to account for the much reduced level of thickening achieved by known inverse emulsion copolymer thickeners in acidic, rather than in alkaline, solutions. In alkaline solutions, functional groups such as $CO_2H$ or $SO_3H$ along the polymer chain are deprotonated to form their charged equivalents $CO_2^-$ and $SO_3^-$, which then repel each other to extend or swell the copolymer structure. In acidic solution, however, such groups as these remain in their protonated forms, reducing the tendency of the copolymer structure to extend or swell. It is therefore quite common for thickeners known in the art to thicken well under alkaline conditions but to display almost no thickening capability at all in acid media. Since some consumer and industrial products, an example being hard surface cleaners for surfaces susceptible to a build-up of limescale deposits, are acidic, rather than alkaline, in nature, thickeners active under acid as well as alkaline conditions are useful within the art.

Consequently, there is a need within the art for inverse emulsion copolymer thickeners that display adequate thickening in both pure water and water containing dissolved salts, that show thickening activity in acidic as well as in alkaline or neutral solutions, and that employ as carrier oil a hydrophobic organic liquid derived from renewable resources rather than from petroleum.

U.S. Pat. No. 4,626,363 teaches the use of inverse emulsion copolymers for thickening of brine, but does not disclose the nature of the carrier oils used in its inverse emulsions. Instead, it cites three other publications. The first, U.S. Pat. No. 3,284,393, describes inverse emulsion copolymerisations using either xylene or perchloroethylene as hydrophobic carriers, neither of which is derived from renewable resources such as plants. The second, U.S. Pat. No. 3,826,771, employs the petroleum-derived isoparaffin Isopar M as the carrier oil in its inverse emulsions. The third, U.S. Pat. No. 4,077,930, employs a variety of petroleum-derived carrier oils, including Mentor 28 (a high boiling paraffinic oil) and what the inventors call "mineral spirits". None of these carrier oils is available from bio-derived or other renewable resources.

U.S. Pat. No. 7,956,012 discloses inverse emulsion copolymers for viscosifying brines used in oilfield applications. The carrier oil employed in the preparation of its inverse emulsions is Shellsol D, described by its supplier as "aliphatic mineral spirits".

U.S. Pat. No. 8,419,976 discloses the combination of an anionic copolymer and a cationic copolymer to thicken aqueous salt solutions. Not all of the copolymers it discloses, however, are inverse emulsion copolymers, and, where inverse emulsion copolymers have been used, the patent is silent as to the nature of the carrier oil they contain.

U.S. patent application Ser. No. 09/888,441 (published as US2002/0032243) discloses inverse emulsion copolymers for use as thickeners in cosmetic, dermocosmetic, dermopharmaceutical or pharmaceutical compositions, the thickeners being demonstrated to thicken 0.1% w/w sodium chloride solutions. These thickeners comprise fatty acid esters, which are in principle derivable from renewable, especially plant, resources, as what the inventors call the "constituent solvent of the oil phase". A study of the example thickeners disclosed reveals, however, that a petroleum-derived mineral oil, Isopar G, is a necessary component in the preparation of these inverse emulsion copolymers.

U.S. patent application Ser. No. 09/849,313 (published as US2001/0051686) and U.S. patent application Ser. No. 09/849,339 (published as US2001/0053801) also disclose inverse emulsion copolymers for use as thickeners in cosmetic, dermocosmetic, dermopharmaceutical or pharmaceutical compositions. The teaching of these two documents is primarily directed towards carrier oils for the inverse emulsion copolymers that are less prone to producing intolerance reactions with some types of sensitive skin within the topical applications for which the thickeners are intended. A number of different carrier oils are shown to be effective in this respect, one of which is squalane, a naturally derived C30 hydrocarbon oil.

US2001/0051686 explicitly discloses a sodium AMPS/acrylamide copolymer cross-linked with MBA, a sodium AMPS homopolymer cross-linked with triallylamine and a sodium AMPS/acrylamide copolymer cross-linked with triallylamine, all prepared as inverse emulsion copolymers having squalane as carrier oil. The efficacy of these copolymers as thickeners is, however, only demonstrated in water. No attempt is made to demonstrate thickening efficiency in aqueous salt solutions.

US2001/0053801 explicitly discloses the lysine salt of an AMPS-acrylic acid copolymer cross-linked with MBA, the monoethanolamine salt of an AMPS-acrylic acid copolymer cross-linked with MBA, and the sodium salt of an AMPS-2-hydroxyethyl acrylate copolymer cross-linked with MBA (three separate examples, differing from each other in the choice of oil-in-water emulsifying surfactant used to invert the composition on addition to aqueous media), all prepared using squalane as the carrier oil. These compositions are all demonstrated to thicken 0.1% w/w aqueous sodium chloride solutions in addition to thickening pure water. The present applicants have found, however, that squalane is only effective as a carrier oil with a limited range of copolymerisable monomers. A number of monomer combinations that will form viable inverse emulsion thickeners with isoparaffinic carrier oils fail to give a viable product when the isoparaffin is replaced by squalane. Furthermore, the present applicants have found that in cases when an apparently stable inverse emulsion copolymer can actually be obtained using squalane as the carrier oil, the viscosity of the inverse emulsion is unworkably high. Such inverse emulsion copolymers would, for instance, be extremely difficult to pump from a storage tank to a mixing vessel on account of their extremely viscous nature. The high viscosities of these inverse emulsions therefore make their use somewhat impractical in an industrial setting. In this context, it is noteworthy that neither US2001/0051686 nor US2001/0053801 disclose the viscosities of their example inverse emulsion copolymer latexes as prepared. Only viscosities in dilute solution/dispersion, typically 3% concentration, are presented.

Therefore, there remains a need within the art for carrier oils derived from renewable resources that are effective with a wide range of ethylenically unsaturated copolymerisable monomers in the preparation of inverse emulsion copolymer thickeners, giving inverse emulsion copolymer latexes of readily handleable/workable viscosities, and the thickeners themselves being effective for the thickening both of pure water and of aqueous solutions or aqueous media containing one or more dissolved salts. Furthermore, such thickeners should ideally display a thickening effect in acidic solutions (having a pH below 6), as well as in alkaline or neutral solutions.

In recent years, 2,6,10-trimethyldodecane, a C15 saturated hydrocarbon, has become available in useful quantities. This material also goes under the common name of farnesane and is commercially available from Amyris Inc. of Emeryville, Calif., USA, under the name Neossance® Hemisqualane. Amyris themselves also sometimes refer to this material as Neossance® TMD. International (PCT) Patent publication number WO 2017/059136 discloses the derivation of farnesane from a fermentation process and advocates its use in the formulation of a wide variety of consumer and industrial products, including personal care products. Amongst the products that farnesane is said to be useful in the preparation of are hard surface heavy duty cleaners, hand cleaners, graffiti removers, crayon/pen ink removers, bug and tar removers, engine degreasers, laundry pre-spotters, oven cleaners, auto interior cleaners, all-purpose cleaner concentrates and metal cleaning fluids, adhesive removers and paint strippers, as well as personal care products such as hair care products, lip care products, skin care products, hygiene products, body care products and sun care products. Paragraphs [0052], [0064] and [0073] of this publication all teach the optional inclusion of a thickener as an additional component in the preparation of any of these product types that also comprise farnesane. However, the publication neither discloses nor anticipates the use of farnesane or any similar fermentation-derived hydrocarbon for the preparation of the thickeners themselves. The publication therefore neither discloses nor anticipates the use of farnesane as the carrier oil in the preparation of inverse emulsion copolymer thickeners useful for the formulation of consumer and industrial products, including personal care products.

Surprisingly, the applicants have found that inverse emulsion copolymer thickeners produced using a carrier oil comprising at least 75% w/w of said carrier oil of farnesane can be prepared with a wider range of ethylenically unsaturated copolymerisable monomers than the inverse emulsion copolymer thickeners comprising a carrier oil of the prior art derived from renewable resources such a fermentation of natural products. In addition, these inverse emulsion copolymer thickeners comprising farnesane have much more user-friendly viscosities than others of the prior art that employ a renewably derived carrier oil, and are also surprisingly more effective at thickening aqueous salt solutions than the other such thickeners according to the prior art. These thickeners comprising farnesane are also surprisingly more effective at thickening acid solutions than others employing petroleum-derived carrier oils of the known art.

Accordingly, in a broad aspect the present invention provides an inverse emulsion copolymer composition comprising an aqueous phase comprising a cross-linked hydrophilic polyelectrolyte copolymer and an oil phase comprising a carrier oil, wherein at least 75% by weight of the carrier oil comprises farnesane (2, 6, 10-trimethyldodecane).

In particular, in a first aspect of the invention the applicants have found that the above-mentioned desirable attributes are exhibited by inverse emulsion copolymer compositions comprising: (A) an aqueous phase comprising a cross-linked hydrophilic polyelectrolyte copolymer (A') obtainable by the free radical copolymerisation of:
  (i) at least one anionic ethylenically unsaturated monomer bearing a negatively charged group and one polymerisable C═C double bond, or at least one cationic ethylenically unsaturated monomer bearing a positively charged group and one polymerisable C═C double bond, and
  (ii) at least one non-ionic ethylenically unsaturated cross-linking monomer bearing at least two polymerisable C═C double bonds, and
  (iii) optionally, one or more hydrophilic non-ionic ethylenically unsaturated monomers bearing one polymerisable C═C double bond, and (B) an oil phase comprising a carrier oil (C), and (D) (i) at least one water-in-oil emulsifying surfactant, and
  (ii) at least one oil-in-water emulsifying surfactant;
characterised in that the carrier oil component (C) of the oil phase (B) comprises from 75% to 100%, by weight of the said carrier oil component (C), of farnesane.

According to preferred embodiments of the invention the composition comprises from 10 to 40% by weight of carrier oil, based on the total of (A)+(B)+(D).

Furthermore, in preferred embodiments of the invention the composition comprises from 10% to 50% by weight of cross-linked hydrophilic polyelectrolyte copolymer (A'), based on the total of (A)+(B)+(D).

A second aspect of the invention concerns the use of an inverse emulsion copolymer composition according to the first aspect for thickening an aqueous medium.

A third aspect of the invention concerns a process for preparing an inverse emulsion copolymer composition according to the first aspect, which process comprises forming a water-in oil emulsion of a monomer composition which contains monomers (A) (i), (A) (ii) and, optionally, (A) (iii) as defined above, and subjecting the monomer composition to inverse emulsion polymerisation in the presence of carrier oil component (C), characterised in that 75% to 100% of the carrier oil component comprises farnesane.

Preferred embodiments of the invention may also include any one or more of the following preferred features. Preferred features mentioned in relation to the first aspect of the invention may apply equally to the second and third aspects.

DETAILED DESCRIPTION OF PREFERRED EMBODIMENTS OF THE INVENTION

As indicated above, the inverse emulsion copolymer compositions of the invention comprise either an anionic or cationic cross-linked polyelectrolyte copolymer (A') dissolved or dispersed in an aqueous phase (A) that is itself dispersed, as a water-in-oil emulsion, in an oil phase (B) comprising a carrier oil (C). Preferably, the inverse emulsion copolymer compositions of the invention comprise from 10% by weight to 40% by weight (based on the weight of the overall composition (A)+(B)+(D)) of the carrier oil component (C). More preferably, the inverse emulsion copolymer compositions of the invention comprise from 12% by weight to 35% by weight (based on the weight of the overall composition (A)+(B)+(D)) of the carrier oil component (C). Most preferably, the inverse emulsion copolymer compositions of the invention comprise from 15% by weight to 30% by weight (based on the weight of the overall composition (A)+(B)+(D)) of the carrier oil component (C). Most especially preferably the inverse emulsion copolymer compositions of the invention comprise from 16% by weight to 26% by weight (based on the weight of the overall composition (A)+(B)+(D)) of the carrier oil component (C).

The carrier oil component (C) of the said oil phase comprises from 75% to 100%, preferably from 80% to 100%, more preferably from 85% to 100%, more preferably still from 90% to 100%, most preferably from 95% to 100%, by weight of the carrier oil component, of farnesane, farnesane being the common name for 2,6,10-trimethyldodecane. It is most especially preferred that 100% of the carrier oil component consists of farnesane.

Where the carrier oil component comprises one or more further carrier oil species (C') in addition to farnesane, it is preferred that these one or more additional carrier oil species (C') are derived, like farnesane, from renewable resources.

Useful examples of renewable resource derived additional carrier oils (C') include alkyl esters, especially lower alkyl ($C_1$-$C_4$ alkyl) esters of fatty acids, the fatty acids typically being derived from plant oils. Examples of such are soybean oil methyl or ethyl ester, linseed oil methyl or ethyl ester, coconut oil methyl or ethyl ester, castor oil methyl or ethyl ester, cottonseed oil methyl or ethyl ester, olive oil methyl or ethyl ester, rapeseed oil methyl or ethyl ester, methyl palmitate, methyl stearate, methyl linoleate, and such like. Fatty acid esters of glycerol (the mono-, di- and especially triglycerides) are also useful. A variety of useful esters of these types is available from IOI Oleo GmbH of Witten, Germany, under the Softenol® trade mark.

More preferred renewable resource derived additional carrier oils (C') include fully saturated hydrocarbons, such as squalane, isosqualane, neosqualane, farnesane dimer, and other fully saturated hydrocarbons described in International Patent Publication no. WO2017/059136.

Less preferred renewable resource derived additional carrier oils (C') include hydrocarbons containing one or more sites of C═C unsaturation, such as hexahydrofarnesene, tetrahydrofarnesene, dihydrofarnesene, or D-limonene.

Even less preferred additional carrier oils (C') are the hydrocarbons derived from petroleum sources, such as isohexadecane, the Hydroseal series of products, including Hydroseal® G232H, Hydroseal® G240H, Hydroseal® G3H and Hydroseal G400H, available in the UK from Banner Chemicals Group of Runcorn, Cheshire, UK, and the Isopar™ range of isoparaffins including Isopar™G, Isopar™H and Isopar™M, offered by ExxonMobil Chemical Europe of Mechelen, Belgium.

It is especially preferred that the inverse emulsion copolymer compositions of the invention are essentially free of petroleum derived isoparaffin hydrocarbons, i.e. they contain less than 1% by weight of petroleum derived isoparaffin hydrocarbons, preferably less than 0.5% and more preferably less than 0.1%.

The inverse emulsion copolymer compositions of the invention comprise an anionic or cationic cross-linked polyelectrolyte copolymer (A') formed in the aqueous phase of the inverse emulsion by a free radical copolymerisation process in which one or more anionic monomer or cationic monomer components (A)(i) is/are copolymerised with a cross-linking monomer component (A)(ii) and, optionally, one or more non-ionic monomer components (A)(iii).

The ionic monomer component (A) (i) may be either anionic or cationic in nature. Embodiments of the invention in which the one or more ionic monomers (A) (i) are anionic monomers are preferred.

Useful anionic monomers are acid functional monomers such as carboxylic acid functional monomers, sulphonic acid functional monomers, phosphoric acid functional monomers and phosphonic acid functional monomers, either in purely acid form, or partially or fully neutralised with one or more bases to convert them, partially or wholly, into the form of their salts.

Preferred acid functional monomers are carboxylic acid functional monomers or sulphonic acid functional monomers, whether in fully acid form or wholly or partly neutralised with base to convert them wholly or partly into their salt form.

Preferred carboxylic acid functional monomers are those bearing one polymerisable C═C double bond and one or more carboxylic acid ($CO_2H$) functional groups. Suitable carboxylic acid functional monomers include acrylic acid, methacrylic acid, β-carboxyethyl acrylate (sometimes referred to as acrylic acid dimer), crotonic acid, glutaconic acid, itaconic acid, fumaric acid, maleic acid and maleic acid anhydride. Acid functional monomers derived from diacids (such as maleic acid) via partial esterification to convert one of the carboxylic acid functional groups to an ester, yielding a monomer bearing one polymerisable C═C double bond and one free carboxylic acid group, may also be used.

The more preferred carboxylic acid functional monomers are those bearing only one carboxylic acid functional group. The most preferred carboxylic acid functional monomers are acrylic acid and methacrylic acid. The most especially preferred carboxylic acid functional monomer is acrylic acid.

Preferred sulphonic acid monomers are those bearing one sulphonic acid group and one polymerisable C═C double bond. These preferred sulphonic acid monomers include vinyl sulphonic acid, allyl sulphonic acid, styrene sulphonic acid, sulphoethyl acrylate, sulphoethyl methacrylate, sulphopropyl acrylate, sulphopropyl methacrylate, 2-hydroxy-3-methacryloxypropyl sulphonic acid, and 2-acrylamido-2-methylpropane sulphonic acid (AMPS). The more preferred sulphonic acid functional monomers are styrene sulphonic acid and 2-acrylamido-2-methylpropane sulphonic acid (AMPS). The most preferred sulphonic acid monomer is 2-acrylamido-2-methylpropane sulphonic acid (AMPS).

As indicated above, in embodiments of the invention in which the ionic monomer component (A) (i) is an anionic, acid functional monomer, the acid functional group may be wholly or partially neutralised with base to give full or partial conversion of the acid group to a salt. Full or partial neutralisation of the acid functional group with one or more bases is preferred over the use of the acid functional monomer in completely free acid form. Full neutralisation of the acid functional group to give complete conversion to the salt form is more preferred.

Suitable bases for full or partial neutralisation of the acid functional group on the monomer component (A) (i) include the common alkalis such as sodium hydroxide, potassium hydroxide and ammonium hydroxide (aqueous ammonia solution), and amine functional bases such as diethylamine, triethylamine, diisopropylamine, triisopropylamine, monoethanolamine, diethanolamine, triethanolamine and 2-amino-2-methyl-1-propanol. Amino acids such as lysine may also be used.

Preferred bases for full or partial neutralisation of the acid functional group on the monomer component (A) (i) are the alkalis sodium hydroxide, potassium hydroxide and ammonium hydroxide (aqueous ammonia solution). Sodium hydroxide and ammonium hydroxide are the more preferred bases.

It therefore follows that, in embodiments of the invention in which the ionic monomer component (A) (i) is an anionic monomer, the anionic monomer component is most preferably selected from (a) sodium or ammonium 2-acrylamido-2-methylpropane sulphonate and (b) sodium or ammonium acrylate, or mixtures thereof. In the most especially preferred embodiments of the invention in which the ionic monomer component (A) (i) is an anionic monomer, the anionic monomer is selected from sodium 2-acrylamido-2-methylpropane sulphonate or a mixture of sodium 2-acrylamido-2-methylpropane sulphonate and sodium acrylate.

In other embodiments of the invention, the ionic monomer component (A) (i) may be a cationic monomer. Preferred cationic monomers include those bearing a quaternary ammonium functional group and one polymerisable C═C double bond.

Useful cationic monomers within the invention are those of general formula (I):

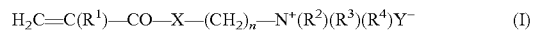

(I)

in which:

$R^1$ is H or $CH^3$, $R^2$, $R^3$ and $R^4$ are each, identically or independently, H or $C_1$-$C_4$ alkyl groups, phenyl groups (—$C_6H_5$) or benzyl groups (—$CH_2C_6H_5$), X is either O or NH, n is an integer from 1 to 4, and Y is a counter ion such as sulphate ($SO_4^-$), nitrate ($NO_3^-$), or chloride ($Cl^-$).

Preferred cationic monomers are those in which:

$R^2$ is H or $CH_3$, $R^2$, $R^3$ and $R^4$ are each independently selected from methyl, ethyl or benzyl groups, X is either O or NH, n is an integer that is either 2 or 3, and Y is a counter ion selected from sulphate ($SO_4^-$) or chloride ($Cl^-$).

More preferably, the cationic monomer is selected from: N,N,N-trimethyl-3-[(2-methyl-1-oxo-2-propenyl)amino]-propanammonium chloride, N,N,N-trimethyl-3-[(1-oxo-2-propenyl)amino]-propanammonium chloride, [2-(methacryloyloxy)ethyl]trimethylammonium chloride, [2-(acryloyloxy)ethyl]trimethylammonium chloride, and [2-(methacryloyloxy)ethyl]dimethylbenzylammonium chloride.

Most preferably, the cationic monomer is [2-(acryloyloxy)ethyl]trimethylammonium chloride.

In compositions in which the ionic monomer component (A) (i) of the aqueous phase (A) is an anionic monomer, the overall monomer composition of the aqueous phase (A) is preferably essentially free of cationic monomer. Likewise, in compositions in which the ionic monomer component (A) (i) of the aqueous phase (A) is a cationic monomer, the overall monomer composition of the aqueous phase (A) is preferably essentially free of anionic monomer.

In this context "essentially free" of a certain class of monomer (whether cationic or anionic) means that the monomer component (A) (i) contains less than 1%, preferably less than 0.5% and most preferably less than 0.1% of that class of monomer. In preferred embodiments the ionic monomer component (A) (i) of the aqueous phase either consists of one or more anionic monomers or consists of one or more cationic monomers.

The cross-linking monomer component A (ii) typically has two or three polymerisable C=C double bonds. These double bonds may be either allylic or (meth)acrylic in character.

Examples of useful allylic-functional cross-linking monomers are diallyl sucrose, diallyl urea, diallyl phthalate, triallyl cyanurate, triallyl isocyanurate, and triallylamine.

Examples of useful (meth)acrylate-functional cross-linking monomers are glycol di(meth)acrylates such as ethylene glycol di(meth)acrylate, 1,6-hexanediol di(meth)acrylate, diethylene glycol di(meth)acrylate, triethylene glycol di(meth)acrylate, the poly[ethylene glycol] di(meth)acrylates; polyol poly(meth)acrylates such as glycerol di(meth)acrylate, glycerol tri(meth)acrylate, trimethylolpropane tri(meth)acrylate, pentaerythritol tri(meth)acrylate, pentaerythritol tetra(meth)acrylate and the ethoxylated and propoxylated derivatives of these polyol poly(meth)acrylates such as ethoxylated trimethylolpropane tri(meth)acrylate, propoxylated glycerol tri(meth)acrylate and the like; and cross-linking monomers derived from acrylamide, such as methylene-bis-acrylamide.

Cross-linking monomers bearing both allylic and (meth)acrylic C=C double bonds, such as allyl (meth)acrylate, may also be used.

Preferably, the cross-linking monomer is selected from triallylamine, triallyl cyanurate, ethoxylated trimethylolpropane tri(meth)acrylate and methylene-bis-acrylamide. Most preferably, the cross-linking monomer is methylene-bis-acrylamide.

The amount of cross-linking monomer used is preferably no less than 1 ppm (parts per million), by weight of the total amount of monomers used, more preferably no less than 100 ppm by weight of the total amount of monomers used, more preferably still no less than 250 ppm by weight of the total amount of monomers used, and most preferably no less than 350 ppm by weight of the total amount of monomers used.

Likewise, the amount of cross-linking monomer used is preferably no more than 4000 ppm (parts per million), by weight of the total amount of monomers used, more preferably no more than 3000 ppm by weight of the total amount of monomers used, more preferably still no more than 2000 ppm by weight of the total amount of monomers used, most preferably no more than 1250 ppm by weight of the total amount of monomers used and most especially preferably no more than 800 ppm by weight of the total amount of monomers used.

The optional non-ionic hydrophilic monomer A (iii) is not particularly limited; any non-ionic monomer having sufficient water solubility or water compatibility to be incorporated into the aqueous phase without undue phase separation may in principle be used.

One useful class of non-ionic hydrophilic monomers is the acrylamide derivatives, including acrylamide, methacrylmide, N-methyl acrylamide, N-methyl methacrylamide and the like.

Another useful class of non-ionic hydrophilic monomers are the lower alkyl acrylates such as methyl acrylate or ethyl acrylate.

Another useful class of non-ionic hydrophilic monomers are the alkyl (meth)acrylate esters bearing one or more hydroxyl substituents on the alkyl group. Examples of these monomers are 2-hydroxyethyl acrylate, hydroxyethyl methacrylate, 2-hydroxypropyl acrylate, hydroxypropyl methacrylate, glycerol monoacrylate, glycerol monomethacrylate, and the polyether mono(meth)acrylates such as the poly[ethylene glycol]mono(meth)acrylates. A number of useful alkyl (meth)acrylate esters bearing a hydroxyl substituent on the alkyl group are available under the Bisomer® trademark from GEO Specialty Chemicals of Southampton, UK, amongst these being Bisomer® PEA6 (a poly[ethylene oxide] monoacrylate having, on average, 6 ethylene oxide units), Bisomer® PEM6 (a poly[ethylene oxide] monomethacrylate having, on average, 6 ethylene oxide units), and Bisomer® PPM5 (a poly[propylene oxide] monomethacrylate having, on average, 5 propylene oxide units).

Other useful non-ionic hydrophilic monomers are N-vinylpyrrolidone, 4-vinylpyridine, and the poly[ethylene glycol] monomethyl ether mono(meth)acrylates which are also available under the Bisomer® trademark from GEO Specialty Chemicals of Southampton, UK.

In embodiments of the invention in which a non-ionic hydrophilic monomer is incorporated into the copolymer compositions of the invention, it is preferred that this monomer is selected from either the group of acrylamide derivatives or the group of alkyl (meth)acrylate esters bearing one or more hydroxyl substituents on the alkyl group.

More preferably, the non-ionic hydrophilic monomer, if used, is selected from acrylamide, methacrylamide, N-methylacrylamide, 2-hydroxyethyl acrylate and hydroxyethyl methacrylate. More preferably, the non-ionic hydrophilic monomer is either absent or is selected from acrylamide, 2-hydroxyethyl acrylate and hydroxyethyl methacrylate. Even more preferably, the non-ionic hydrophilic monomer is either absent or is selected from acrylamide and hydroxyethyl methacrylate.

Most preferably, the optional non-ionic hydrophilic monomer is either absent or is hydroxyethyl methacrylate.

If an optional non-ionic hydrophilic monomer is used, it is preferably used in an amount no less than 1% by weight of the total weight of monomers used. More preferably, it is used in an amount no less than 2.5% by weight of the total monomers used. More preferably still, it is used in an amount no less than 4% by weight of the total monomers used. Most preferably, it is used in an amount no less than 6% by weight of the total monomers used.

Likewise, if an optional non-ionic hydrophilic monomer is used, it is preferably used in an amount no more than 25% by weight of the total weight of monomers used. More preferably, it is used in an amount no more than 22.5% by weight of the total monomers used. More preferably still, it is used in an amount no more than 20% by weight of the total monomers used. Most preferably, it is used in an amount no more than 16% by weight of the total monomers used.

In embodiments of the invention the cross-linked hydrophilic copolymer (A') may be obtained by reacting one ionic ethylenically unsaturated monomer (A) (i) with non-ionic ethylenically unsaturated cross-linking monomer (A) (ii). The hydrophilic polyelectrolyte copolymer (A') thus produced could equally be described by the person skilled in the art as a "cross-linked homopolymer", in view of the fact that the cross-linking monomer is typically the minor component of the monomer starting materials. However, in the context of the present invention, it is designated a "copolymer" (rather than a cross-linked homopolymer) as it is derived from at least two different monomer starting materials.

Conveniently the inverse emulsion copolymer compositions of the invention may comprise from 10% by weight to 50% by weight of cross-linked hydrophilic polyelectrolyte copolymer (A'), (based on the weight of the overall composition (A)+(B)+(D)). In preferred embodiments the compositions may comprise 15% by weight to 45% by weight of cross-linked hydrophilic copolymer, and more preferably 20% to 40% by weight, based on the total of (A), (B) and (D). In certain preferred embodiments, the weight % content of the copolymer (A') is in the range of 30% to 40%, based on the total weight of (A), (B) and (D).

In the most especially preferred embodiments of the invention the cross-linked hydrophilic polyelectrolyte copolymer (A') is obtained by the free radical copolymerisation of monomer combinations comprising or consisting of either:
  (a) Sodium 2-acrylamido-2-methyl-propane sulfonate, hydroxyethyl methacrylate and methylene-bis-acrylamide, or
  (b) Sodium 2-acrylamido-2-methyl-propane sulfonate, sodium acrylate and methylene-bis-acrylamide, or
  (c) Sodium 2-acrylamido-2-methyl-propane sulfonate and methylene-bis-acrylamide, or
  (d) [2-(Acryloyloxy)ethyl]trimethylammonium chloride and methylene-bis-acrylamide.

The inverse emulsion copolymers (A') of the invention are prepared by a free radical emulsion polymerisation in inverse emulsion. Such a process may generally involve dissolving monomers (A) (i), (A) (ii) and, optionally, (A) (iii) in aqueous solution; combining the aqueous solution with carrier oil component (C) and surfactant (D) (i) to form a water-in-oil emulsion; performing free radical polymerisation to form a cross-linked hydrophilic polyelectrolyte copolymer (A') in the inverse (water-in-oil) emulsion; and adding surfactant (D) (ii) to provide an inverse emulsion copolymer thickener.

In a typical process, the aqueous phase of the inverse emulsion is prepared separately from the oil phase of the inverse emulsion, prior to being stirred into the oil phase and the mixture then being homogenised under conditions of high shear. The free radical polymerisation process is then commenced by adding all or part of a free radical initiating system at a temperature ranging from 15° C. to 25° C., preferably from 18° C. to 22° C. The polymerisation reaction is exothermic, so leads to a rise in temperature of the mixture up to 40° C. to 70° C., more commonly up to 50° C. to 60° C. Once the exotherm has peaked, heating is applied to the reaction to raise the temperature up to 75° C.-90° C., preferably up to 75° C.-85° C., more preferably up to 75° C.-82° C. After a period at this temperature, further amounts of free radical initiators are added to ensure completion of the polymerisation reaction before the inverse emulsion is cooled down to less than 45° C., more preferably less than 40° C., when the oil-in-water emulsifying surfactant (often called the "inverting surfactant") is stirred in. The finished product is then further cooled down to normal ambient temperature and decanted through a filter to remove any coagulum ("grit"). Nylon mesh of 80μ, preferably 60μ, mesh size is a particularly useful filter material.

In the above process, the aqueous phase is typically prepared by dispensing a weighed amount of deionised water into a suitable vessel and stirring the chosen monomers into it to make a solution. In cases in which one or more of the chosen monomers is commercially supplied as a pre-prepared solution, the initial amount of deionised water dispensed into the vessel may be small, or even none at all.

In cases in which one or more of the chosen monomers is an anionic, acid functional monomer and it is desired to utilise some or all of this acidic monomer in the form of one of its salts, the monomer salt solution may be pre-prepared in a different vessel, or may be commercially available, ready to use, in the salt form. Alternatively, in cases in which one or more of the chosen monomers is an anionic, acid functional monomer and it is desired to utilise some or all of this acidic monomer in the form of one of its salts, the acidic monomer may first be dissolved or dispersed in the initial amount of deionised water in the vessel and the required amount of neutralising base cautiously stirred in, if necessary with cooling to avoid excessive temperature rise.

Optionally, a chelating agent may be included in the aqueous phase. Tetrasodium ethylenediamine tetraacetate and pentasodium diethylene triamine pentaacetate are useful chelating agents, with pentasodium diethylene triamine pentaacetate being preferred.

The oil phase of the typical process is commonly prepared by dispensing the required amount of carrier oil into the reaction vessel and dissolving in it an amount of one or more water-in-oil emulsifying surfactants (Di) to provide a total amount of water-in oil emulsifying surfactant(s) in the range 0.1% to 8% by weight, preferably 0.5% to 6.0%, more preferably 1.0% to 4.0%, even more preferably 1.25% to 3% by weight, and most preferably 1.5% to 2.5% by weight of the composition as a whole, (A)+(B)+(D).

Useful water-in-oil emulsifying surfactants include the sorbitan esters sorbitan oleate, sorbitan isostearate and sorbitan sesqioleate (all of which are commercially available from Seppic of Castres, France, under the trade name Montane™), and the esters of polyalkoxylated sorbitan, such as the monooleate of pentaethoxylated sorbitan and the isostearate of pentaethoxylated sorbitan (also available from Seppic under the trade name Montanox™). Another useful class of water-in-oil emulsifying surfactants is the fatty acid amide type of surfactant such as Simaline™ IE2000 (available from Seppic, as above) or Witcamide™ 511 (available from Akzo Nobel Surface Chemistry of Stenungsund, Sweden).

It will also be appreciated by the skilled reader that, as the water-in-oil emulsifying surfactant is dissolved in the carrier oil in an initial stage when preparing the oil phase, then the water-in-oil emulsifying surfactant (D) (i) is not strictly present in the inverse emulsion copolymer composition containing cross-linked hydrophilic polyelectrolyte copolymer (A') as an independent component, separate from the oil phase. However, as is customary in this field, the water-in-oil emulsifying surfactants (D) (i) are listed as components separate from the oil phase (B). In this specification, in cases where weight ranges are proposed for the oil phase (B), the calculated weight ranges do not include amounts for the water-in-oil emulsifying surfactants (D) (i), nor do they include the amounts for oil-in-water emulsifying surfactants.

In preferred embodiments of the invention, the water-in-oil emulsifying surfactant is selected from sorbitan monooleate, a mixture of sorbitan monooleate and the aforementioned Simaline™ IE2000, or the aforementioned Witcamide™ 511.

The free radical polymerisation reaction is normally activated by a free radical initiator system. The preferred initiator system is a so-called "redox couple" of two complementary initiators that are added to the reactor separately but which act together to effect polymerisation.

One component of the redox couple is an oxidant component. Useful oxidant components are the persulphate salts such as ammonium persulphate, sodium persulphate or potassium persulphate, a hydroperoxide such as tertiary butyl hydroperoxide or cumene hydroperoxide, or potassium bromate.

The other component of the redox couple is a reductant component. Useful reductant components are sodium metabisulphite, sodium hydrosulphite, tartaric acid, ascorbic acid, or a ferrous salt such as ferrous sulphate. At one time, sodium formaldehyde sulfoxylate (SFS) was a very popular reductant component. More recently, however, this has fallen out of favour on account of its tendency to liberate formaldehyde during use. On account of this, alternatives to SFS are beginning to be introduced into the market by initiator suppliers. One such is Bruggolite® FF6, offered by Bruggemann Chemicals of Heilbronn, Germany, a particularly useful reductant component whose precise composition is not available within the public domain.

Usually, the oxidant component of the redox couple is added to the homogenised emulsion as a single shot. It may even be the case that the oxidant component is incorporated into the preparation of the aqueous phase prior to emulsification. The reductant component is then gradually metered in as a drip-feed.

The final step in the preparation of the inverse emulsion copolymer is the addition of the so-called "inverting surfactant". In principle, any non-ionic surfactant with a HLB value sufficiently high to promote oil-in-water emulsification may be used. In the earlier years of inverse emulsion copolymer thickener technology, alkoxylated alkylphenols, especially ethoxylated nonylphenols, were popular choices as inverting surfactants, but these have now fallen out of favour on account of environmental concerns. Various different surfactant types have found utility as alternatives to nonylphenol ethoxylates, though their precise chemistries are not always available within the public domain. Amongst these various alternative inverting surfactants may be listed the various ethoxylated castor oil derivatives, and the ethoxylated $C_{10}$-$C_{20}$ aliphatic alcohols. The ethoxylated $C_{10}$-$C_{20}$ aliphatic alcohols are preferred.

Oil-in-water emulsifying surfactant(s) are preferably added in an amount ranging from 0.1% to 8.0%, preferably 0.5% to 6%, more preferably 1.0 to 4.0%, most preferably 1.5% to 3.5%, based on the total of (A)+(B)+(D).

Example inverse emulsion copolymer compositions illustrating the present invention have shown effective thickening in neutral compositions having a pH of about 7 and in alkaline solutions which have a pH of about 8, for example. Excellent thickening has also been observed for the compositions acidic formulations having a pH of about 6 or lower and including those as acidic as pH 1.

Embodiments of the present invention will now be illustrated by the following examples.

EXAMPLES

Materials

The sodium AMPS solution used in these examples was the commercial product AMPS® 2405 Monomer, a 58% aqueous solution of sodium 2-acrylamido-2-methyl-propane sulfonate supplied by Lubrizol France of Rouen.

The aqueous solution of acrylamide used in these examples was the commercial product Acrylamide 50% LC-NA, supplied by Kemira Oyj of Helsinki, Finland.

Adamquat® MC80 is an aqueous solution of 2-(acryloxy) ethyl trimethylammonium chloride of concentration 70%-85%, available from Arkema France.

"Caustic Solution 70TW" is a 32% aqueous solution of sodium hydroxide available from Univar of Bradford, UK.

Dissolvine D40 is a 40% aqueous solution of pentasodium diethylene triamine pentaacetate available from Akzo Nobel Functional Chemicals of Arnhem, the Netherlands.

The farnesane used in these examples was Neossance® Hemisqualane, supplied by Amyris Inc. of Emeryville, Calif., USA.

The squalane used in these examples was Neossance® Squalane, also supplied by Amyris Inc. of Emeryville, Calif., USA.

Span 80 is a commercial grade of sorbitan monooleate offered by Croda Europe Ltd. of Goole, UK. This is a water-in-oil emulsifying surfactant.

Witcamide 511 is a proprietary fatty acid amide surfactant available from Akzo Nobel Surface Chemistry AB of Stenungsund, Sweden. This is a water-in-oil emulsifying surfactant.

Simaline IE 2000 is a proprietary fatty amide surfactant available from Seppic S. A. of Paris, France. This is a water-in-oil emulsifying surfactant.

Bruggolite FF6 is a proprietary reducing agent available from Bruggemann Chemicals of Heilbronn, Germany. Its chemical nature is a trade secret.

Trigonox K90 is a proprietary grade of cumene hydroperoxide available from Akzo Nobel Functional Chemicals of Amersfoort, The Netherlands.

Lanspec EMP102 is an ethoxylated alcohol surfactant available from Lankem Ltd. of Dukinfield, Cheshire, UK. This is an oil-in-water emulsifying surfactant.

Surfaline SE60 is a proprietary non-ionic surfactant described as "polysorbate 60" by its supplier, Ceca Arkema of La Garenne-Colombes, France. This is an oil-in-water emulsifying surfactant.

PREPARATIVE EXAMPLES

Example 1 (Inventive): A sodium 2-acrylamido-2-methyl-1-propane sulfonate+hydroxyethyl methacrylate Copolymer Cross-Linked with methylene-bis-acrylamide in Inverse Emulsion Using Farnesane as Carrier Oil First the aqueous phase of the inverse emulsion was prepared, starting by charging 599.78 g of sodium AMPS solution to a stainless steel beaker of 1-litre capacity. This solution was then stirred using a stainless steel circular toothed blade powered by a variable speed electric stirrer motor while 20.00 g of hydroxyethyl methacrylate was gradually added from a small glass beaker. This beaker was then rinsed into the stirred mixture with 7.328 g deionised water. 0.141 g of methylene-bis-acrylamide was weighed out onto a small piece of aluminium foil and added to the stirred mixture, the foil then being rinsed into the mixture with 12.00 g of deionised water. This was followed by a solution of 0.471 g of Dissolvine D40 dissolved in 10.00 g deionised water from a small beaker, which was then rinsed into the stirred mixture with 10.00 g of deionised water. The pH of the stirred mixture was measured by pH meter and adjusted, if necessary, to within the range 4.0 to 4.5 by adding drops of acrylic acid from a pipette. The amount of acrylic acid added during this step was noted; in this case it was 4.00 g. This completed the preparation of the aqueous phase.

229.484 g of farnesane was charged to a jacketed glass reactor of capacity 2 litres. The jacket enabled heating or cooling of the vessel via a water (hot or cold) inlet and outflow. 21.00 g of Span 80 was also added, following which a stainless steel paddle-type stirrer was positioned within the reactor contents and the vessel lidded. As well as a central port to accommodate the stirrer shaft, the glass lid was also fitted with a condenser and other ports to accommodate a nitrogen gas inlet, a stainless steel thermocouple for monitoring the temperature of the reactor contents throughout the process, the tube feed (0.8 mm internal diameter tubing) from a peristaltic pump and a dropping funnel. While feeding a strong flow of nitrogen through the vessel, the contents were stirred at 300 rpm for 10 minutes to dissolve the Span 80 in the farnesane carrier oil. After this, the nitrogen flow was backed off to a more modest rate and the stirrer speed reduced to 150 rpm before the aqueous phase prepared above was gradually fed into the farnesane/Span 80 solution via the dropping funnel. The dropping funnel was then rinsed into the reactor with deionised water, the amount of deionised water used for this being 12.50 g minus the quantity of any acrylic acid noted as used to adjust the pH of the aqueous phase, so in this case 8.50 g. Stirring was continued for a further 10 minutes before being stopped. The lid and stirrer were removed and the open reactor transferred to a Silverson high shear stirrer, a device familiar to those skilled in the art. Cold water was fed through the reactor jacket to mitigate against excessive temperature rise during homogenisation, and the mixture homogenised by high shear stirring at 5000 rpm with the Silverson for 5 minutes. As a check to ensure satisfactory homogenisation, the viscosity of the resulting mixture was checked with a Brookfield viscometer operating on spindle 4 at 20 rpm; a viscosity below 400 centipoise under these conditions is usually indicative of an unstable emulsion which could break down during polymerisation, leading to gelation of the whole batch before completion of the reaction. Should a viscosity below 400 centipoise be observed, this number can sometimes be raised by further time under Silverson shear stirring; however, in this case, the viscosity after 5 minutes was 440 centipoise.

After removing from the Silverson, the original paddle stirrer was replaced in the reactor and the lid, with the same range of ports and fitted inlets, dropping funnel, etc., refitted. The batch was stirred at 150 rpm for 90 minutes while purging with nitrogen. The reactor's water jacket was also used to stabilise the batch temperature to 21±1° C., in this case 21.6° C. In separate small beakers, 0.211 g of ammonium persulphate was dissolved in 4.00 g of deionised water and 0.066 g of Trigonox K90 was dissolved in 7.90 g of farnesane. These solutions were added, one after the other, to the contents of the reactor. 2.00 g of a 10% w/w solution of Bruggolite FF6 was fed into the stirred reactor contents using the peristaltic pump feed at a rate of 0.065 ml/minute. Polymerisation was evidenced by a rapid rise in batch temperature. After 37 minutes the batch temperature peaked at 56.4° C., following which the remainder of the FF6 solution was fed in at the maximum rate the pump was capable of delivering while the water jacket of the reactor was used to heat the reactor contents to 85° C. and stabilise at that temperature ±1° C. At 85° C., a further 9.00 g of 10% w/w Bruggolite FF6 solution was added via the peristaltic pump at a rate of 0.3 ml/minute. After completion of this feed, the reactor contents were stirred for 1 hour at 85+1° C. to ensure completion of the polymerisation reaction. After this time, the reactor's water jacket was switched to cold water feed and the contents of the reactor cooled with stirring to <35° C. before 33.70 g of Surfaline SE60 surfactant were added and stirred in. The resulting inverse emulsion copolymer thickener was discharged from the reactor through a 60μ mesh size nylon filter to remove any coagulum. The inverse emulsion copolymer thus obtained had a viscosity (Brookfield, spindle 3 speed 20 rpm) of 17 Poise after equilibrating at 25° C. in a thermostated water bath.

The inverse emulsion copolymer thickener composition of Example 1 contains 38.0% copolymer (A'), 24.2% farnesane, 2.14% water-in-oil emulsifying surfactant and 3.44% oil-in-water emulsifying surfactant. All the percentages are by weight based on the total amounts of (A)+(B)+(D).

Example 2 (Comparative): A sodium 2-acrylamido-2-methyl-1-propane sulfonate+hydroxyethyl methacrylate Copolymer Cross-Linked with methylene-bis-acrylamide in Inverse Emulsion Using Squalane as Carrier Oil The procedure set out above for Example 1 was repeated, but replacing any farnesane used in Example 1 with squalane. In this case, however, the Brookfield viscosity of the water-in-oil emulsion obtained in the Silverson homogenisation step could not be raised above 170 centipoise. Initiator additions commenced at 20.0° C. During the initial FF6 solution feed, the batch temperature peaked at 56.9° C. after 30 minutes but gelation was observed at this stage and it was impossible to continue with the remaining steps of the process. The batch therefore had to be dumped before it went completely solid.

Example 3 (Inventive): A sodium 2-acrylamido-2-methyl-1-propane sulfonate+sodium acrylate Copolymer Cross-Linked with methylene-bis-acrylamide in Inverse Emulsion Using Farnesane as Carrier Oil First the aqueous phase of the inverse emulsion was prepared, starting by charging 432.31 g of sodium AMPS solution to a stainless steel beaker of 1-litre capacity, this solution then being stirred using a stainless steel circular toothed blade powered by a variable speed electric stirrer motor. 0.120 g of methylene-bis-acrylamide was weighed out onto a small piece of aluminium foil and added to the stirred mixture, the foil then being rinsed into the mixture with 9.98 g of deionised water. This was followed by a solution of 0.43 g of Dissolvine D40 dissolved in 8.31 g deionised water from a small beaker, which was then rinsed into the stirred mixture with a further 8.31 g of deionised water. 103.59 g of acrylic acid was poured into the stirred solution and 179.84 g of Caustic Solution 70TW added very gradually, so as to maintain a solution temperature below 30° C. The pH of the stirred mixture was measured by pH meter and adjusted, if necessary, to within the range 5.6 to 5.8 by adding drops of acrylic acid from a pipette. The amount of acrylic acid added during this step was noted; in this case it was 18.66 g. This completed the preparation of the aqueous phase.

174.280 g of farnesane was charged to a jacketed glass reactor of capacity 2 litres. The jacket enabled heating or cooling of the vessel via a water (hot or cold) inlet and outflow. 21.68 g of Span 80 was also added, following which a stainless steel paddle-type stirrer was positioned within the reactor contents and the vessel lidded. As well as a central port to accommodate the stirrer shaft, the glass lid was also fitted with a condenser and other ports to accommodate a nitrogen gas inlet, a stainless steel thermocouple for monitoring the temperature of the reactor contents throughout the process, the tube feed (0.8 mm internal diameter tubing) from a peristaltic pump and a dropping funnel. While feeding a strong flow of nitrogen through the vessel, the contents were stirred at 300 rpm for 10 minutes to dissolve the Span 80 in the farnesane carrier oil. After this, the nitrogen flow was backed off to a more modest rate and the stirrer speed reduced to 150 rpm before the aqueous phase prepared above was gradually fed into the farnesane/Span 80 solution via the dropping funnel. The dropping funnel was then rinsed into the reactor with 16.63 g of deionised water. Stirring was continued for a further 10 minutes before being stopped. The lid and stirrer were removed and the open reactor transferred to a Silverson high shear stirrer, a device familiar to those skilled in the art. Cold water was fed through the reactor jacket to mitigate against excessive temperature rise during homogenisation, and the mixture homogenised by high shear stirring at 5000 rpm with the Silverson for 5 minutes. As a check to ensure satisfactory homogenisation, the viscosity of the resulting mixture was checked with a Brookfield viscometer operating on spindle 4 at 20 rpm; a viscosity below 400 centipoise under these conditions is usually indicative of an unstable emulsion which could break down during polymerisation, leading to gelation of the whole batch before completion of the reaction. Should a viscosity below 400 centipoise be observed, this number can sometimes be raised by further time under Silverson shear stirring; however, in this case, the viscosity after 5 minutes was 1680 centipoise.

After removing from the Silverson, the original paddle stirrer was replaced in the reactor and the lid, with the same range of ports and fitted inlets, dropping funnel, etc., refitted. The batch was stirred at 150 rpm for 90 minutes while purging with nitrogen. The reactor's water jacket was also used to stabilise the batch temperature to 20±1° C., in this case 20.1° C. In separate small beakers, 0.210 g of ammonium persulphate was dissolved in 4.00 g of deionised water and 0.067 g of Trigonox K90 was dissolved in 10.00 g of deionised water. These solutions were added, one after the other, to the contents of the reactor. 4.00 g of a 10% w/w solution of Bruggolite FF6 was fed into the stirred reactor contents using the peristaltic pump feed at a rate of 0.123 ml/minute. Polymerisation was evidenced by a rapid rise in batch temperature. After 22 minutes the batch temperature peaked at 70° C., following which the remainder of the FF6 solution was fed in at the maximum rate the pump was capable of delivering while the water jacket of the reactor was used to heat the reactor contents to 80° C. and stabilise at that temperature ±1° C. At 80° C., a further 6.00 g of 10% w/w Bruggolite FF6 solution was added via the peristaltic pump at a rate of 0.6 ml/minute. After completion of this feed, the reactor contents were stirred for 1 hour at 80+1° C. to ensure completion of the polymerisation reaction. After this time, the reactor's water jacket was switched to cold water feed and the contents of the reactor cooled with stirring to <35° C. before 21.00 g of Lanspec EMP 102 surfactant were added and stirred in. The resulting inverse emulsion copolymer thickener was discharged from the reactor through a 60p mesh size nylon filter to remove any coagulum. The inverse emulsion copolymer thus obtained had a viscosity (Brookfield, spindle 3 speed 20 rpm) of 20 Poise at 25° C.

The inverse emulsion copolymer thickener composition of Example 3 contains 37.6% copolymer (A'), 17.1% farnesane, 2.13% water-in-oil emulsifying surfactant and 2.06% oil-in-water emulsifying surfactant. All the percentages are by weight based on the total amounts of (A)+(B)+(D).

Example 4 (Comparative): A sodium
2-acrylamido-2-methyl-1-propane sulfonate+sodium
acrylate Copolymer Cross-Linked with
methylene-bis-acrylamide in Inverse Emulsion
Using Squalane as Carrier Oil The procedure according to Example 3 was repeated, but replacing the farnesane used with squalane. The viscosity of the homogenised emulsion could only be raised to 60 centipoise, however, and the batch gelled only three minutes after the commencement of the FF6 solution feed. No perceptible temperature rise had occurred during that time.

Example 5 (Inventive): A sodium
2-acrylamido-2-methyl-1-propane Sulfonate
Homopolymer Cross-Linked with
methylene-bis-acrylamide in Inverse Emulsion
Using Farnesane as Carrier Oil First the aqueous phase of the inverse emulsion was prepared, starting by charging 599.78 g of sodium AMPS solution to a stainless steel beaker of 1-litre capacity, along with 7.328 g deionised water. This solution was then stirred using a stainless steel circular toothed blade powered by a variable speed electric stirrer motor. 0.141 g of methylene-bis-acrylamide was weighed out onto a small piece of aluminium foil and added to the stirred mixture, the foil then being rinsed into the mixture with 12.00 g of deionised water. This was followed by a solution of 0.471 g of Dissolvine D40 dissolved in 10.00 g deionised water from a small beaker, which was then rinsed into the stirred mixture with 10.00 g of deionised water. The pH of the stirred mixture was measured by pH meter and adjusted, if necessary, to within the range 5.6 to 5.9 by adding drops of acrylic acid from a pipette. The amount of acrylic acid added during this step was noted; in this case, it was 0.6 g. This completed the preparation of the aqueous phase.

229.484 g of farnesane was charged to a jacketed glass reactor of capacity 2 litres. The jacket enabled heating or cooling of the vessel via a water (hot or cold) inlet and outflow. 21.00 g of Span 80 was also added, following which a stainless steel paddle-type stirrer was positioned within the reactor contents and the vessel lidded. As well as a central port to accommodate the stirrer shaft, the glass lid was also fitted with a condenser and other ports to accommodate a nitrogen gas inlet, a stainless steel thermocouple for monitoring the temperature of the reactor contents throughout the process, the tube feed (0.8 mm internal diameter tubing) from a peristaltic pump and a dropping funnel. While feeding a strong flow of nitrogen through the vessel, the contents were stirred at 300 rpm for 10 minutes to dissolve the Span 80 in the farnesane carrier oil. After this, the nitrogen flow was backed off to a more modest rate and the stirrer speed reduced to 150 rpm before the aqueous phase prepared above was gradually fed into the farnesane/Span 80 solution via the dropping funnel. The dropping funnel was then rinsed into the reactor with deionised water, the amount of deionised water used for this being 12.50 g minus the quantity of any acrylic acid noted as used to adjust the pH of the aqueous phase, so in this case 11.90 g. Stirring was continued for a further 10 minutes before being stopped. The lid and stirrer were removed and the open reactor transferred to a Silverson high shear stirrer, a device familiar to those skilled in the art. Cold water was fed through the reactor jacket to mitigate against excessive temperature rise during homogenisation, and the mixture homogenised by high shear stirring at 5000 rpm with the Silverson for 5 minutes. As a check to ensure satisfactory homogenisation, the viscosity of the resulting mixture was checked with a Brookfield viscometer operating on spindle 4 at 20 rpm; a viscosity below 400 centipoise under these conditions is usually indicative of an unstable emulsion which could break down during polymerisation, leading to gelation of the whole batch before completion of the reaction. Should a viscosity below 400 centipoise be observed, this number can sometimes be raised by further time under Silverson shear stirring; however, in this case, the viscosity after 5 minutes was 450 centipoise.

After removing from the Silverson, the original paddle stirrer was replaced in the reactor and the lid, with the same range of ports and fitted inlets, dropping funnel, etc., refitted. The batch was stirred at 150 rpm for 90 minutes while purging with nitrogen. The reactor's water jacket was also used to stabilise the batch temperature to 21±1° C., in this case 20.7° C. In separate small beakers, 0.211 g of ammonium persulphate was dissolved in 4.00 g of deionised water and 0.066 g of Trigonox K90 was dissolved in 7.90 g of farnesane. These solutions were added, one after the other, to the contents of the reactor. 2.00 g of a 10% w/w solution of Bruggolite FF6 was fed into the stirred reactor contents using the peristaltic pump feed at a rate of 0.065 ml/minute. Polymerisation was evidenced by a rapid rise in batch temperature. After 16 minutes the batch temperature peaked at 56.8° C., following which the remainder of the FF6 solution was fed in at the maximum rate the pump was capable of delivering while the water jacket of the reactor was used to heat the reactor contents to 85° C. and stabilise at that temperature ±1° C. At 85° C., a further 9.00 g of 10% w/w Bruggolite FF6 solution was added via the peristaltic pump at a rate of 0.3 ml/minute. After completion of this feed, the reactor contents were stirred for 1 hour at 85+1° C. to ensure completion of the polymerisation reaction. After this time, the reactor's water jacket was switched to cold water feed and the contents of the reactor cooled with stirring to <35° C. before 33.70 g of Surfaline SE60 surfactant were added and stirred in. The resulting inverse emulsion copolymer thickener was discharged from the reactor through a 60p mesh size nylon filter to remove any coagulum. The inverse emulsion copolymer thus obtained had a viscosity (Brookfield, spindle 3 speed 20 rpm) of 14.2 Poise at 25° C.

The inverse emulsion copolymer thickener composition of Example 5 contains 36.3% copolymer (A'), 24.7% farnesane, 2.18% water-in-oil emulsifying surfactant and 3.50% oil-in-water emulsifying surfactant. All the percentages are by weight based on the total amounts of (A)+(B)+(D).

Example 6 (Comparative): A sodium
2-acrylamido-2-methyl-1-propane Sulfonate
Homocopolymer Cross-Linked with
methylene-bis-acrylamide in Inverse Emulsion
Using Squalane as Carrier Oil The procedure according to Example 5 was repeated, but replacing the farnesane used with squalane. The viscosity after homogenisation was 5330 centipoise. The reaction was initiated at 22.1° C. and the resulting exotherm raised the temperature to 55.3° C. in 25 minutes. The inverse emulsion copolymer thus obtained was, however, extremely viscous, too viscous to measure by the usual technique.

Example 7 (Inventive): A sodium
2-acrylamido-2-methyl-1-propane sulfonate+methyl
acrylate Copolymer Cross-Linked with
methylene-bis-acrylamide in Inverse Emulsion
Using Farnesane as Carrier Oil The procedure according to Example 1 was repeated, but replacing the hydroxyethyl methacrylate used with methyl acrylate. The viscosity of the homogenised emulsion was 420 centipoise. The reaction was initiated at 19.1° C. and the peak exotherm temperature of 54.6° C. was reached after 26 minutes. The remainder of the process continued satisfactorily to give an inverse emulsion copolymer having a Brookfield viscosity (spindle 3 speed 20 rpm) of 25 Poise at 25° C.

The inverse emulsion copolymer thickener composition of Example 7 contains 38.0% copolymer (A'), 24.2% farnesane, 2.14% water-in-oil emulsifying surfactant and 3.44% oil-in-water emulsifying surfactant. All the percentages are by weight based on the total amounts of (A)+(B)+(D).

Example 8 (Comparative): A sodium
2-acrylamido-2-methyl-1-propane sulfonate+methyl
acrylate Copolymer Cross-Linked with
methylene-bis-acrylamide in Inverse Emulsion
Using Squalane as Carrier Oil The procedure according to Example 1 was repeated, but replacing the hydroxyethyl methacrylate used with methyl acrylate and replacing the farnesane used with squalane. The viscosity after homogenisation was 2400 centipoise. The reaction was initiated at 21.1° C. and the resulting exotherm raised the temperature to 55.7° C. in 32 minutes. The inverse emulsion copolymer thus obtained was, however, like Example 6, extremely viscous, too viscous to measure by the usual technique.

Example 9 (Inventive): A Ammonium Acrylate
Homopolymer Cross-Linked with
methylene-bis-acrylamide in Inverse Emulsion
Using Farnesane as Carrier Oil First the aqueous phase of the inverse emulsion was prepared, starting by charging 268.98 g of deionised water to a stainless steel beaker of 1-litre capacity, this then being stirred using a stainless steel circular toothed blade powered by a variable speed electric stirrer motor. 0.60 g of methylene-bis-acrylamide was weighed out onto a small piece of aluminium foil and added to the stirred mixture, the foil then being rinsed into the mixture with 30.00 g of deionised water. This was followed by a solution of 0.50 g of Dissolvine D40 dissolved in 10.00 g deionised water from a small beaker, which was then rinsed into the stirred mixture with a further 10.00 g of deionised water. 206.77 gg of acrylic acid was poured into the stirred solution and 119.86 g of ammonia solution (S.G.=0.880) added very gradually, so as to maintain a solution temperature below 30° C. The pH of the stirred mixture was measured by pH meter and adjusted, if necessary, to within the range 5.4 to 5.6 by adding drops of ammonia solution (same as above) from a pipette. The amount of ammonia solution added during this step was noted; in this case it was 5.16 g. This completed the preparation of the aqueous phase.

225.66 g of farnesane was charged to a jacketed glass reactor of capacity 2 litres. The jacket enabled heating or cooling of the vessel via a water (hot or cold) inlet and outflow. 25.00 g of Witcamide 511 was also added, following which a stainless steel paddle-type stirrer was positioned within the reactor contents and the vessel lidded. As well as a central port to accommodate the stirrer shaft, the glass lid was also fitted with a condenser and other ports to accommodate a nitrogen gas inlet, a stainless steel thermocouple for monitoring the temperature of the reactor contents throughout the process, the tube feed (0.8 mm internal diameter tubing) from a peristaltic pump and a dropping funnel. While feeding a strong flow of nitrogen through the vessel, the contents were stirred at 300 rpm for 10 minutes to dissolve the Witcamide in the farnesane carrier oil. After this, the nitrogen flow was backed off to a more modest rate and the stirrer speed reduced to 150 rpm before the aqueous phase prepared above was gradually fed into the farnesane/Witcamide solution via the dropping funnel. The dropping funnel was then rinsed into the reactor with deionised water, the amount of deionised water used for this being 50.00 g minus the quantity of any ammonia solution noted as used to adjust the pH of the aqueous phase, so in this case 44.84 g. Stirring was continued for 90 minutes while purging with nitrogen before being stopped. The lid and stirrer were removed and the open reactor transferred to a Silverson high shear stirrer, a device familiar to those skilled in the art. Cold water was fed through the reactor jacket to mitigate against excessive temperature rise during homogenisation, and the mixture homogenised by high shear stirring with the Silverson at 600 rpm for 5 minutes, then at 4800 rpm for 5 minutes. As a check to ensure satisfactory homogenisation, the viscosity of the resulting mixture was checked with a Brookfield viscometer operating on spindle 3 at 20 rpm; a viscosity below 400 centipoise under these conditions is usually indicative of an unstable emulsion which could break down during polymerisation, leading to gelation of the whole batch before completion of the reaction. Should a viscosity below 400 centipoise be observed, this number can sometimes be raised by further time under Silverson shear stirring; however, in this case, the viscosity after 15 minutes was 765 centipoise.

After removing from the Silverson, the original paddle stirrer was replaced in the reactor and the lid, with the same range of ports and fitted inlets, dropping funnel, etc., refitted. The reactor's water jacket was also used to stabilise the batch temperature to 22±1° C., in this case 21.1° C. 0.20 g of ammonium persulphate was dissolved in 4.00 g of deionised water in a small beaker and added to the contents of the reactor. After 2 minutes, feeding was commenced of a solution of 0.05 g of sodium metabisulphite in 9.98 g of deionised water, using the peristaltic pump feed at a rate of 0.167 ml/minute. Polymerisation was evidenced by a rapid rise in batch temperature. After 105 minutes the batch temperature peaked at 62.4° C., following which the water jacket of the reactor was used to heat the reactor contents to 90° C. and stabilise at that temperature ±1° C. for 30 minutes. After this time, solutions of 0.4 g ammonium persulphate in 3.8 g deionised water and 0.4 g sodium metabisulphite in 3.8 g deionised water were added to the reactor and stirring continued at 90° C. for a further 30 minutes to ensure completion of the polymerisation reaction. After this time, the reactor's water jacket was switched to cold water feed and the contents of the reactor cooled with stirring to <25° C. before 30.00 g of Lanspec EMP 102 surfactant were added and stirred in. The resulting inverse emulsion copolymer thickener was discharged from the reactor through a 60µ mesh size nylon filter to remove any coagulum. The inverse emulsion copolymer thus obtained had a viscosity (Brookfield, spindle 3 speed 20 rpm) of 21 Poiseat 25° C.

The inverse emulsion copolymer thickener composition of Example 9 contains 20.7% copolymer (A'), 22.6% farnesane, 2.50% water-in-oil emulsifying surfactant and 3.00% oil-in-water emulsifying surfactant. All the percentages are by weight based on the total amounts of (A)+(B)+(D).

Example 10 (Comparative): A Ammonium Acrylate Homopolymer Cross-Linked with methylene-bis-acrylamide in Inverse Emulsion Using Squalane as Carrier Oil The procedure according to Example 9 was repeated, but replacing the farnesane used with squalane. The viscosity after homogenisation was 2350 centipoise and the polymerisation reaction initiated at 22.0° C. During polymerisation, the reaction exotherm raised the temperature of the batch to a peak of 65.7° C. 47 minutes after commencement of the sodium metabisulphite solution feed. The inverse emulsion copolymer thus obtained was, however, extremely viscous, in a similar way to Examples 6 and 8, having a viscosity too great to measure by the usual technique.

Example 11 (Comparative): A Ammonium Acrylate Homopolymer Cross-Linked with methylene-bis-acrylamide in Inverse Emulsion Using a 50:50 Mixture of Farnesane and Squalane as Carrier Oil The procedure according to Example 9 was repeated, but replacing 112.83 g of the farnesane used with 112.83 g of squalane. It was necessary to add a further 13.2 g of ammonia solution to the aqueous phase to raise the pH to 5.40. The viscosity after homogenisation was 1700 centipoise and the polymerisation reaction initiated at 23.0° C. During polymerisation, the reaction exotherm raised the temperature of the batch to a peak of 64.9° C. 62 minutes after commencement of the sodium metabisulphite solution feed. The inverse emulsion copolymer thus obtained had a viscosity (Brookfield, spindle 3 speed 20 rpm) of 40 Poise at 25° C.

Example 12 (Inventive): A Ammonium Acrylate Homopolymer Cross-Linked with methylene-bis-acrylamide in Inverse Emulsion Using a 75:25 Mixture of Farnesane and Squalane as Carrier Oil The procedure according to Example 9 was repeated, but replacing 56.41 g of the farnesane used with 56.41 g of squalane. It was necessary to add a further 17.3 g of ammonia solution to the aqueous phase to raise the pH to 5.54. The viscosity after homogenisation was 1580 centipoise and the polymerisation reaction initiated at 21.1° C. During polymerisation, the reaction exotherm raised the temperature of the batch to a peak of 61.8° C. 69 minutes after commencement of the sodium metabisulphite solution feed. The inverse emulsion copolymer thus obtained had a viscosity (Brookfield, spindle 3 speed 20 rpm) of 20 Poise at 25° C.

The inverse emulsion copolymer thickener composition of Example 12 contains 20.7% copolymer (A'), 22.6% farnesane, 2.50% water-in-oil emulsifying surfactant and 3.00% oil-in-water emulsifying surfactant. All the percentages are by weight based on the total amounts of (A)+(B)+(D).

Example 13 (Inventive): A 2-(acryloxy)ethyl trimethylammonium chloride+acrylamide Copolymer Cross-Linked with methylene-bis-acrylamide in Inverse Emulsion Using Farnesane as Carrier Oil First the aqueous phase of the inverse emulsion was prepared, starting by charging 98.91 g of deionised water, 430.00 g of Adamquat MC80 and 122.00 g of a 50% aqueous solution of acrylamide to a stainless steel beaker of 1-litre capacity. This solution was then stirred using a stainless steel circular toothed blade powered by a variable speed electric stirrer motor. 0.150 g of methylene-bis-acrylamide was weighed out onto a small piece of aluminium foil and added to the stirred mixture, the foil then being rinsed into the mixture with 10.00 g of deionised water. This was followed by a solution of 0.94 g of Dissolvine D40 dissolved in 10.00 g deionised water from a small beaker, which was then rinsed into the stirred mixture with 10.00 g of deionised water. Finally, 8.00 g acrylic acid was added. The pH of the stirred mixture was measured by pH meter and adjusted, if necessary, to within the range 4.0 to 4.3 by adding drops of acrylic acid from a pipette. Once the pH had been shown to lie within the required range, a solution of 0.20 g of potassium bromate in 5.00 g deionised water was added from a small beaker, the beaker being rinsed into the mixture afterwards with a further 10.00 g of deionised water. This completed the preparation of the aqueous phase.

225.00 g of farnesane was charged to a jacketed glass reactor of capacity 2 litres. The jacket enabled heating or cooling of the vessel via a water (hot or cold) inlet and outflow. 23.00 g of Span 80 and 2.00 g of Simaline IE 2000 were also added, following which a stainless steel paddle-type stirrer was positioned within the reactor contents and the vessel lidded. As well as a central port to accommodate the stirrer shaft, the glass lid was also fitted with a condenser and other ports to accommodate a nitrogen gas inlet, a stainless steel thermocouple for monitoring the temperature of the reactor contents throughout the process, the tube feed (0.8 mm internal diameter tubing) from a peristaltic pump and a dropping funnel. While feeding a strong flow of nitrogen through the vessel, the contents were stirred at 300 rpm for 10 minutes to dissolve the two surfactants in the farnesane carrier oil. After this, the nitrogen flow was backed off to a more modest rate and the stirrer speed reduced to 150 rpm before the aqueous phase prepared above was gradually fed into the farnesane/surfactant solution via the dropping funnel. Stirring at this speed was continued for 2 hours while purging the mixture with nitrogen. The lid and stirrer were then removed and the open reactor transferred to a Silverson high shear stirrer, a device familiar to those skilled in the art. Cold water was fed through the reactor jacket to mitigate against excessive temperature rise during homogenisation, and the mixture homogenised by high shear stirring at 4800 rpm for 15 minutes. As a check to ensure satisfactory homogenisation, the viscosity of the resulting mixture was checked with a Brookfield viscometer operating on spindle 3 at 20 rpm; a viscosity below 450 centipoise under these conditions is usually indicative of an unstable emulsion which could break down during polymerisation, leading to gelation of the whole batch before completion of the reaction. Should a viscosity below 450 centipoise be observed, this number can sometimes be raised by further time under Silverson shear stirring; however, in this case, the viscosity after 15 minutes was 950 centipoise.

After removing from the Silverson, the original paddle stirrer was replaced in the reactor and the lid, with the same range of ports and fitted inlets, dropping funnel, etc., refitted. The reactor's water jacket was used to stabilise the batch temperature to 19±1° C., in this case 20.0° C. A solution of 0.50 g sodium metabisulphite in 10.00 g deionised water was then fed into the stirred reactor contents using the peristaltic pump feed at a rate of 0.111 ml/minute. Polymerisation was evidenced by a rapid rise in batch temperature. After 53 minutes the batch temperature peaked at 71.1° C., following which the water jacket of the reactor was used to heat the reactor contents to 80° C. and stabilise at that temperature +1° C. After 30 minutes stirring at 80° C., solutions of 0.20 g ammonium persulphate in 2.00 g deionised water and 0.20 g sodium metabisulphite in 2.00 g deionised water were added to the reactor one after the other. A further 0.20 g ammonium persulphate in 1.00 g deionised water was then added, followed 15 minutes later by a further 0.20 g of sodium metabisulphite in 1.00 g deionised water. After a further 15 minutes a solution of 0.50 g sodium metabisulphite in 2.00 g deionised water was added and stirring continued at 80° C. for 30 more minutes to ensure completion of the polymerisation reaction. After this time, the reactor's water jacket was switched to cold water feed and the contents of the reactor cooled with stirring to <25° C. before 25.00 g of Lanspec E102 surfactant were added and stirred in. The resulting inverse emulsion copolymer thickener was discharged from the reactor through a 60μ mesh size nylon filter to remove any coagulum. The inverse emulsion copolymer thus obtained had a viscosity (Brookfield, spindle 3 speed 20 rpm) of 12 Poise at 25° C.

The inverse emulsion copolymer thickener composition of Example 13 contains 40.2% copolymer (A'), 22.5% farnesane, 2.50% water-in-oil emulsifying surfactant and 2.50% oil-in-water emulsifying surfactant. All the percentages are by weight based on the total amounts of (A)+(B)+(D).

Example 14 (Comparative): A 2-(acryloxy)ethyl trimethylammonium chloride+acrylamide Copolymer Cross-Linked with methylene-bis-acrylamide in Inverse Emulsion Using Squalane as Carrier Oil The procedure according to Example 13 was repeated, but replacing the farnesane used with squalane. The viscosity of the emulsion after the homogenisation step was 17,000 centipoise. The polymerisation reaction was initiated at 20.8° C. and the exotherm peaked 30 minutes after commencement of the sodium metabisulphite solution feed at 56.3° C. As with Examples 6, 8 and 10, however, the inverse emulsion copolymer obtained was extremely viscous, having a viscosity too great to determine by the usual method.

Example 15 (Inventive): A 2-(acryloxy)ethyl trimethylammonium Chloride Homopolymer Cross-Linked with methylene-bis-acrylamide in Inverse Emulsion Using Farnesane as Carrier Oil First the aqueous phase of the inverse emulsion was prepared, starting by charging 259.57 g of deionised water and 419.79 g of Adamquat MC80 to a stainless steel beaker of 1-litre capacity. This solution was then stirred using a stainless steel circular toothed blade powered by a variable speed electric stirrer motor. 0.150 g of methylene-bis-acrylamide was weighed out onto a small piece of aluminium foil and added to the stirred mixture, the foil then being rinsed into the mixture with 7.68 g of deionised water. This was followed by a solution of 0.92 g of Dissolvine D40 dissolved in 7.68 g deionised water from a small beaker, which was then rinsed into the stirred mixture with 7.68 g of deionised water. The pH was recorded (6.0) but not adjusted. This completed the preparation of the aqueous phase.

215.89 g of farnesane was charged to a jacketed glass reactor of capacity 2 litres. The jacket enabled heating or cooling of the vessel via a water (hot or cold) inlet and outflow. 15.35 g of Span 80 was also added, following which a stainless steel paddle-type stirrer was positioned within the reactor contents and the vessel lidded. As well as a central port to accommodate the stirrer shaft, the glass lid was also fitted with a condenser and other ports to accommodate a nitrogen gas inlet, a stainless steel thermocouple for monitoring the temperature of the reactor contents throughout the process, the tube feed (0.8 mm internal diameter tubing) from a peristaltic pump and a dropping funnel. While feeding a strong flow of nitrogen through the vessel, the contents were stirred at 300 rpm for 5 minutes to dissolve the Span 80 in the farnesane carrier oil. After this, the nitrogen flow was backed off to a more modest rate and the stirrer speed reduced to 150 rpm before the aqueous phase prepared above was gradually fed into the farnesane/surfactant solution via the dropping funnel, the drained funnel being flushed into the reactor with 7.68 g of deionised water. Stirring continued at 150 rpm for 2 hours while purging the mixture with nitrogen. The lid and stirrer were then removed and the open reactor transferred to a Silverson high shear stirrer, a device familiar to those skilled in the art. Cold water was fed through the reactor jacket to mitigate against excessive temperature rise during homogenisation, and the mixture homogenised by high shear stirring at 4800 rpm for 15 minutes. As a check to ensure satisfactory homogenisation, the viscosity of the resulting mixture was checked with a Brookfield viscometer operating on spindle 3 at 20 rpm; a viscosity below 450 centipoise under these conditions is usually indicative of an unstable emulsion which could break down during polymerisation, leading to gelation of the whole batch before completion of the reaction. Should a viscosity below 450 centipoise be observed, this number can sometimes be raised by further time under Silverson shear stirring; however, in this case, the viscosity after 5 minutes was 1225 centipoise.

After removing from the Silverson, the original paddle stirrer was replaced in the reactor and the lid, with the same range of ports and fitted inlets, dropping funnel, etc., refitted. The reactor's water jacket was used to stabilise the batch temperature to 19±1° C. 0.20 g of 2,2-azo-bis-isobutyronitrile was added via a powder funnel, followed by a solution of 0.07 g Trigonox K90 in 7.97 g farnesane. A solution of 0.05 g sodium metabisulphite in 25.23 g deionised water was then fed into the stirred reactor contents using the peristaltic pump feed at a rate of 0.422 ml/minute. Polymerisation was evidenced by a rapid rise in batch temperature. After 64 minutes the batch temperature peaked at 50.0° C., following which the water jacket of the reactor was used to heat the reactor contents to 80° C. and stabilise at that temperature ±1° C. After 30 minutes stirring at 80° C., a further 0.10 g of 2,2-azo-bis-isobutyronitrile was added to ensure completion of the polymerisation reaction. After this, the reactor's water jacket was switched to cold water feed and the contents of the reactor cooled with stirring to <25° C. before 23.99 g of Lanspec E102 surfactant were added and stirred in. The resulting inverse emulsion copolymer thickener was discharged from the reactor through a 60μ mesh size nylon filter to remove any coagulum. The inverse emulsion copolymer thus obtained had a viscosity (Brookfield, spindle 3 speed 20 rpm) of 15 Poise at 25° C.

The inverse emulsion copolymer thickener composition of Example 15 contains 32.5% copolymer (A'), 22.4% farnesane, 1.53% water-in-oil emulsifying surfactant and 2.40% oil-in-water emulsifying surfactant. All the percentages are by weight based on the total amounts of (A)+(B)+(D).

Example 16 (Comparative): A 2-(acryloxy)ethyl trimethylammonium Chloride Homopolymer Cross-Linked with methylene-bis-acrylamide in Inverse Emulsion Using Squalane as Carrier Oil The procedure of Example 15 was repeated, but replacing the farnesane used with squalene. In this case, homogenisation only raised the viscosity of the mixture to 150 centipoise, but nevertheless a viable inverse emulsion copolymer was ultimately obtained. The polymerisation reaction was initiated at 19.8° C. and the peak reaction exotherm temperature was 48.9° C., occurring 39 minutes after commencement of the initiator feed. In common, however, with Examples 6, 8, 10 and 14, each of which also employed squalane exclusively as the carrier oil, the inverse emulsion copolymer obtained had an extremely high viscosity, too high to measure by the usual method.

Evaluation of Thickening Effectiveness

The thickening effectiveness of the various inverse emulsion copolymers was determined in both deionised water and 3% w/w sodium chloride solution.

386 g (±0.1 g) of deionised water at normal indoor ambient temperature was dispensed into a 600 ml plastic beaker and 12.0 g (±0.05 g) of the inverse emulsion copolymer under test added it. Using a stainless steel circular toothed blade powered by a variable speed electric stirrer motor, the mixture was stirred under high shear for 2 minutes before its viscosity was measured using a Brookfield, model DV-1 viscometer fitted with spindle 6 rotating at 5 rpm.

After recording this, the DI Water Viscosity, in centipoise (dPa·s), 2.0 g (±0.05 g) of a solution of 20% w/w sodium chloride in deionised water was added to the mixture in the beaker with continuous stirring, and high shear stirring again applied for a period of 2 minutes. The Brookfield viscosity was measured again, this time using spindle 4 at 5 rpm, this being the 3% Salt Viscosity.

Inverse emulsion copolymer Examples 1, 3, 5, 6, 7 and 8 were evaluated by this test method and the results are set out in Table I. (Examples 2 and 4, both of which employed squalane as carrier oil component (C), were not available for test, having gelled into a solid mass during their attempted preparation.)

TABLE I

| Anionic Monomer (A) (i) | Sodium AMPS | Sodium AMPS + sodium acrylate | Sodium AMPS | | Sodium AMPS | |
|---|---|---|---|---|---|---|
| Crosslinker (A) (ii) | | | Methylene-bis-acrylamide | | | |
| Non-ionic Monomer (A) (iii) | HEMA | None | None | | Methyl acrylate | |
| EXAMPLE No. | 1 | 3 | 5 | 6 | 7 | 8 |
| Carrier Oil (C) | Farnesane | Farnesane | Farnesane | Squalane | Farnesane | Squalane |
| Bulk Viscosity (Poise) | 17.0 | 20.0 | 14.2 | Excessive | 25.0 | Excessive |
| DI Water Viscosity (dPa · s) | 804 | 636 | 880 | 258 | 860 | 524 |
| 3% Salt Viscosity (dPa · s) | 243 | 204 | 134 | 50 | 39.4 | 77.6 |

Sodium AMPS = sodium 2-acrylamido-2-methyl-propane sulfonate.
HEMA = Hydroxyethyl methacrylate.

The data in Table I show three particularly noteworthy features: The two Examples employing squalane as the carrier oil component (C) both had excessively high bulk viscosities, so would be difficult products to handle in an industrial manufacturing setting.

The two Examples employing squalane as the carrier oil component (C) are also the two showing the lowest DI Water Viscosities. Squalane is the oil of plant origin mentioned in some of the prior art documents discussed herein.

The three Examples showing the highest 3% Salt Viscosities all employ farnesane as the carrier oil component (C).

Inverse emulsion copolymer Examples 9, 10, 11 and 12 were also subjected to the same evaluation procedure. These four Examples all contained the same copolymer, obtained via the copolymerisation of ammonium acrylate and methylene-bis-acrylamide. The difference between them is in the carrier oil component (C). The results are set out in Table II.

TABLE II

| | EXAMPLE No. | | | |
|---|---|---|---|---|
| | 9 | 10 | 11 | 12 |
| Carrier oil (C) | 100% Farnesane | 100% Squalane | 50% Farnesane 50% Squalane | 75% Farnesane 25% Squalane |
| Bulk Viscosity (Poise) | 21.0 | Excessive | 40.0 | 20.0 |
| DI Water Viscosity (dPa · s) | 1830 | 1020 | 1200 | 1910 |
| 3% Salt Viscosity (dPa · s) | 193 | 38 | 6 | 115 |

The data in Table II show a clear trend in 3% Salt Viscosity improvement as the squalane content of the carrier oil component (C) is reduced and the farnesane content is correspondingly increased.

The four Examples in which the ionic monomer (A) (i) is a cationic monomer, Examples 13, 14, 15 and 16, were also subjected to thickening efficiency evaluation by the same procedure. The results are set out in Table III.

TABLE III

| Cationic Monomer (A) (i) | 2-(Acryloxy)ethyl trimethylammonium chloride | | | |
|---|---|---|---|---|
| Cross-linker (A) (ii) | Methylene-bis-acrylamide | | | |
| Non-ionic monomer (A) (iii) | Acrylamide | | None | |
| EXAMPLE No. | 13 | 14 | 15 | 16 |
| Carrier oil (C) | Farnesane | Squalane | Farnesane | Squalane |
| Bulk Viscosity (Poise) | 12.0 | Excessive | 14.2 | Excessive |
| DI Water Viscosity (dPa · s) | 688 | 878 | 880 | 258 |
| 3% Salt Viscosity (dPa · s) | 140 | 94.4 | 218 | 19.6 |

As with the anionic copolymer formulations that are the subject of Tables I and II, the cationic copolymer compositions of Table III are also of such high bulk viscosity if employing squalane as carrier oil component (C), according to the prior art, that they would be impractical to handle in an industrial manufacturing setting. Examples 13 and 15, which employ farnesane as carrier oil component (C), also show greater thickening efficiency in 3% salt solutions than do their counterpart Examples 14 and 16, which employ the squalane carrier oil component (C) of the prior art.

Overall, the above illustrative Examples show, therefore, that inverse emulsion copolymer thickeners employing predominantly or exclusively farnesane as the carrier oil of the inverse emulsion can be prepared with a wider range of copolymerisable monomers than those that employ squalene as carrier oil according to the prior art, giving compositions having much more readily handleable bulk viscosities than their squalane equivalents and typically functioning more effectively as thickeners for salt containing aqueous solutions than their squalane based equivalents.

The inverse emulsion copolymer compositions of the invention are particularly suitable for use as thickeners for personal care products, cosmetics, and other products intended for topical application.

USE EXAMPLES

Example 17: Preparation of an Aftershave Balm

| A | Inverse emulsion of Example 1 | 1.50% |
|---|---|---|
|   | Water | 82.80% |
| B | Micropearl™ M 100 | 5.00% |
|   | Sepicide™ CI | 0.50% |
|   | Fragrance | 0.20% |
|   | 95° ethanol | 10.00% |

Procedure: Add B to A under high shear stirring.

Example 18: Preparation of an Oil-in-Water Cream

| A | Simulsol™ 165 | 5.00% |
|---|---|---|
|   | Lanol™ 1688 | 20.00% |
|   | Lanol™ P | 1.00% |
| B | Water |   |
| C | Inverse emulsion of Example 3 | 2.50% |
| D | Sepicide™ CI | 0.20% |
|   | Sepicide™ HB | 0.30% |

Procedure: Heat the three items A to 70-75° C. and mix together with gentle stirring. Heat item B to 70-75° C. and introduce gradually into A under high shear stirring. Cool to 55° C. and stir in C under high shear. Finally cool further, to 45° C. and incorporate items D, also under high shear stirring.

Example 19: Preparation of a Massage Gel

| A | Inverse emulsion of Example 5 | 3.50% |
|---|---|---|
|   | Water | 20.00% |
| B | Dye solution | 2 drops/100 g |
|   | Water | 61.40% |
| C | 95° ethanol | 10.00% |
|   | Menthol | 0.10% |
| D | Silicone oil (350 cS) | 5.00% |

Procedure: Under high speed stirring, gradually add the inverse emulsion to the water of part A. Separately, dissolve the dye solution in the water of part B and stir this solution into part A under high shear. Likewise, dissolve the menthol in the ethanol and stir this solution into the mixture, followed by the silicone oil.

Micropearl™ M 100 is a proprietary grade of poly[methyl methacrylate] microspheres sold by the company Matsumo.

Sepicide™ CI is a proprietary imidazolineurea preservative sold by the company SEPPIC.

Sepicide™ HB is a proprietary paraben/phenoxyethanol preservative sold by the company SEPPIC.

Simulsol™ 165 is a proprietary non-ionic surfactant, a mixture of esters of glycerol and ethoxylated glycerol, sold by the company SEPPIC.

Lanol™ 1688 is a proprietary liquid emollient ester sold by the company SEPPIC.

Lanol™ P is also a proprietary emollient ester sold by the company SEPPIC.

Examples 20-22: Preparation of a Skin Care Gel

The numbers in Table IV are amounts in parts by weight.

TABLE IV

| PHASES | INGREDIENT | EXAMPLE 20 | EXAMPLE 21 | EXAMPLE 22 |
|---|---|---|---|---|
| A | Cetearyl alcohol | 5.0 | 5.0 | 5.0 |
|   | Glyceryl stearate | 2.0 | 2.0 | 2.0 |
|   | Dicaprylyl ether | 2.0 | 2.0 | 2.0 |
|   | Isostearyl isostearate | 5.0 | 5.0 | 5.0 |
| B | Dimethicone | 5.0 | 5.0 | 5.0 |
| C | Water | 75.9 | 75.9 | 75.9 |
|   | Glycerine | 2 | 2 | 2 |
| D | Example 1 | 1.2 | — | — |
|   | Example 3 | — | 1.2 | — |
|   | Example 5 | — | — | 1.2 |
| E | Pentylene glycol | 1.0 | 1.0 | 1.0 |
|   | Caprylyl glycol | 0.7 | 0.7 | 0.7 |
|   | Tocopherol acetate | 0.2 | 0.2 | 0.2 |

Cetearyl alcohol was obtained as Crodacol™ 1618 from Croda Personal Care of Goole, East Yorks, UK.

Glyceryl stearate was obtained as Cithrol™ GMS 40 SE from Evonik, of Essen, Germany.

Dicapryl ether was obtained as Cetiol™ OE from the global network of BASF.

Isostearyl isostearate was obtained as DUB ISIS™ from Stearinerie Dubois, of Boulogne, France.

Dimethicone is a Dow Corning product, Silicone DC 200 (350 cst). The glycerine was a cosmetic grade supplied as Glycon™ G 100 by Lonza AG, of Basle, Switzerland.

Pentylene glycol was supplied as Hydrolite™-5 616751 by Symrise Ltd., of Marlow, Bucks., UK.

Caprylyl glycol was supplied as Hydrolite™-8 109169, also by Symrise Ltd.

Tocopherol acetate was supplied as Onynex™ K, a BASF product.

The Phase A materials were heated together at 70° C. with gentle stirring until complete dissolution was achieved. Phase B was then stirred in slowly. Phase C was heated to 75° C. and then emulsified into the A+B mixture at 70° C. with increased agitation. After cooling to 50° C., Phase D was slowly stirred in and further cooling applied to reduce the temperature to 40° C. before stirring in Phase E.

The properties of Examples 20 to 22 are set out in Table V.

TABLE V

| PROPERTY | EXAMPLE 20 | EXAMPLE 21 | EXAMPLE 22 |
|---|---|---|---|
| Appearance | White, gel-like and shining emulsion. | White, gel-like and shining emulsion. | White, gel-like and shining emulsion. |
| Brookfield Viscosity (spindle 4 speed 6 rpm). | 25,000 cps | 20,000 cps | 22,000 cps |
| pH | 7.0 | 7.5 | 7.0 |
| Stability (one month at room temperature). | Stable | Stable | Stable |

Examples 23-25: Preparation of a Skin Care Day Cream

The numbers in Table VI are amounts in parts by weight

TABLE VI

| PHASES | INGREDIENT | EXAMPLE 23 | EXAMPLE 24 | EXAMPLE 25 |
|---|---|---|---|---|
| A | Cetearyl alcohol | 5.0 | 5.0 | 5.0 |
|   | Glyceryl stearate | 2.0 | 2.0 | 2.0 |
|   | Caprylic/capric triglyceride | 4.0 | 4.0 | 4.0 |
|   | Octyldecanol | 2.0 | 2.0 | 2.0 |
|   | Isononyl isononanoate | 16.0 | 16.0 | 16.0 |
| B | Water | 66.8 | 66.8 | 66.8 |
|   | Glycerine | 2.0 | 2.0 | 2.0 |
| C | Example 1 | 0.5 | — | — |
|   | Example 3 | — | 0.5 | — |
|   | Example 5 | — | — | 0.5 |
| D | Pentylene glycol | 1.0 | 1.0 | 1.0 |
|   | Caprylyl glycol | 0.7 | 0.7 | 0.7 |

Caprylic/capric triglyceride was obtained a DUB MCT™ 5545 from Stearinerie Dubois, of Boulogne, France.

Octyldecanol was supplied as Eutanol™ G, a BASF product.

The Phase A materials were heated together at 70° C. with gentle stirring until complete dissolution was achieved. Phase B was then emulsified with Phase A over 10 minutes at 70° C. with increased agitation. After cooling to 60° C., Phase C was slowly stirred in and further cooling applied to reduce the temperature to 40° C. before stirring in Phase D.

The properties of Examples 23 to 25 are set out in Table VII.

TABLE VII

| PROPERTY | EXAMPLE 23 | EXAMPLE 24 | EXAMPLE 25 |
|---|---|---|---|
| Appearance | White, creamy and shining emulsion. | White, creamy and shining emulsion. | White, creamy and shining emulsion. |
| Brookfield Viscosity (spindle 4 speed 6 rpm). | 21,000 cps | 21,000 cps | 18,000 cps |
| pH | 7.5 | 6.5 | 6.6 |
| Stability (one month at room temperature). | Stable | Stable | Stable |

Examples 26-28: Preparation of a Sun Protection Cream

The numbers in Table VIII are amounts in parts by weight

TABLE VIII

| PHASES | INGREDIENT | EXAMPLE 26 | EXAMPLE 27 | EXAMPLE 28 |
|---|---|---|---|---|
| A | Water | 42.75 | 42.75 | 42.75 |
|   | Xanthan gum | 0.15 | 0.15 | 0.15 |
|   | Tetrasodium EDTA | 0.20 | 0.20 | 0.20 |
|   | Glycerine | 4.00 | 4.00 | 4.00 |
|   | Triethanolamine | 1.00 | 1.00 | 1.00 |
|   | Phenylbenzimidazole sulfonic acid | 3.00 | 3.00 | 3.00 |
| B | Isodecyl neopentanoate | 17.00 | 17.00 | 17.00 |
|   | Ethylhexyl salicilate | 5.00 | 5.00 | 5.00 |
|   | Isopropyl isostearate | 3.00 | 3.00 | 3.00 |
|   | Ethylhexyl methoxycinnamate (Octinoxate) | 6.00 | 6.00 | 6.00 |
|   | Butyl methoxydibenzoylmethane (Avobenzone) | 3.00 | 3.00 | 3.00 |
| C | Cetearyl alcohol | 5.00 | 5.00 | 5.00 |
|   | Glyceryl stearate | 2.00 | 2.00 | 2.00 |
| D | Example 1 | 1.00 | — | — |
|   | Example 3 | — | 1.00 | — |
|   | Example 5 | — | — | 1.00 |
| E | Cyclomethicone | 5.00 | 5.00 | 5.00 |
|   | Pentylene glycol | 1.00 | 1.00 | 1.00 |
| F | Caprylyl glycol | 0.70 | 0.70 | 0.70 |
|   | Tocopherol acetate | 0.20 | 0.20 | 0.20 |

The Xanthan gum used was Keltrol™ CG T, a product of CP Kelco ApS of Lille Skensved, Denmark.

The phenylbenzimidazole used was Eusolex™ 232, a product of Merck KGaA of Darmstadt, Germany.

Isodecyl neopentanoate was obtained a DUB VCI™ 10 and isopropyl isostearate as DUB ISIP™, both from Stearinerie Dubois, of Boulogne, France.

Ethyl salicylate was obtained as Eusolex™ OS, a product of Merck KGaA of Darmstadt, Germany.

Butyl methoxydibenzoylmethane was obtained as Eusolex™ 9020, also a product of Merck KGaA of Darmstadt, Germany.

The ethylhexyl methoxycinnamate used was Uvinul™ MC 80, a product of the BASF worldwide network.

The cyclodimethicone used was the Dow Corning product DC 345.

The xanthan gum was first dispersed in the water before mixing in the other Phase A ingredients. The Phase B ingredients were mixed together in a separate vessel until homogeneous. Phase C was dissolved in Phase B at 75° C. with gentle stirring, before this mixture was emulsified into Phase A at 75° C. with light agitation. After cooling to 40° C., Phases D, E and F were added in sequence, with stirring continuing while the product cooled down to 23° C.

The properties of the sun protection creams are set out in Table IX

TABLE IX

| PROPERTY | EXAMPLE 26 | EXAMPLE 27 | EXAMPLE 28 |
|---|---|---|---|
| Appearance | White, shining emulsion. | White, shining emulsion. | White, shining emulsion. |
| Brookfield Viscosity (spindle 4 speed 6 rpm). | 20,000 cps | 20,000 cps | 30,000 cps |
| pH | 8.1 | 8.1 | 8.0 |
| Stability (one month at room temperature). | Stable | Stable | Stable |

Examples 29-31: Preparation of a Foundation Cream

The numbers in Table X are amounts in parts by weight

TABLE X

| PHASES | INGREDIENT | EXAMPLE 29 | EXAMPLE 30 | EXAMPLE 31 |
|---|---|---|---|---|
| A | Water | 44.16 | 44.16 | 44.16 |
|   | Xanthan gum | 0.15 | 0.15 | 0.15 |
|   | Tetrasodium EDTA | 0.20 | 0.20 | 0.20 |
|   | Propylene glycol | 7.00 | 7.00 | 7.00 |
|   | Triethanolamine | 1.00 | 1.00 | 1.00 |
| B | Red iron oxide pigment paste | 0.24 | 0.24 | 0.24 |
|   | Black iron oxide pigment paste | 0.05 | 0.05 | 0.05 |
|   | Yellow iron oxide pigment paste | 1.80 | 1.80 | 1.80 |
|   | Titanium dioxide pigment paste | 4.50 | 4.50 | 4.50 |
|   | Propylene glycol | 6.00 | 6.00 | 6.00 |
| C | Cetearyl alcohol | 5.00 | 5.00 | 5.00 |
|   | Glyceryl stearate | 2.00 | 2.00 | 2.00 |
|   | Isodecyl neopentanoate | 20.00 | 20.00 | 20.00 |
| D | Example 1 | 1.00 | — | — |
|   | Example 3 | — | 1.00 | — |
|   | Example 5 | — | — | 1.00 |
| E | Cyclomethicone | 5.00 | 5.00 | 5.00 |
| F | Pentylene glycol | 1.00 | 1.00 | 1.00 |
|   | Caprylyl glycol | 0.70 | 0.70 | 0.70 |
|   | Tocopherol acetate | 0.20 | 0.20 | 0.20 |

The propylene glycol was obtained from Interchimie of Compans, France.

The triethanolamine was a product of the BASF worldwide network. The various pigment pastes were supplied under the Covacrine trade name by Sensient Cosmetic Technologies of Saint Ouen L'Aumone, France.

The xanthan gum was dispersed in the water before mixing in the other Phase A ingredients. The Phase B ingredients were mixed together in a different vessel and added into Phase A with moderate agitation. The Phase C ingredients were dissolved together at 75° C. and the hot solution emulsified into A+B with vigorous agitation. After cooling to 50° C., Phase D was stirred in and further cooling applied. At 40° C., Phases E and F were stirred in.

The properties of these foundation creams are set out in Table XI.

TABLE XI

| PROPERTY | EXAMPLE 29 | EXAMPLE 30 | EXAMPLE 31 |
|---|---|---|---|
| Appearance | White, shining emulsion. | White, shining emulsion. | White, shining emulsion. |
| Brookfield Viscosity (spindle 4 speed 6 rpm). | 35,000 cps | 20,000 cps | 23,000 cps |
| pH | 6.8 | 7.1 | 7.1 |
| Stability (one month at room temperature). | Stable | Stable | Stable |

FURTHER SYNTHETIC EXAMPLES

The following Comparative Examples 32 to 37 were prepared using the paraffinic oils Isopar M or isohexadecane. These hydrocarbons were adopted as the preferred carrier oils in many of the prior art documents discussed herein.

Example 32 (Comparative): A sodium 2-acrylamido-2-methyl-1-propane sulfonate+hydroxyethyl methacrylate Copolymer Cross-Linked with methylene-bis-acrylamide in Inverse Emulsion Using Isopar M as Carrier Oil The procedure according to Example 1 was repeated, only replacing the 229.484 g of farnesane with 229.484 g of Isopar M.

Example 33 (Comparative): A sodium 2-acrylamido-2-methyl-1-propane sulfonate+hydroxyethyl methacrylate Copolymer Cross-Linked with methylene-bis-acrylamide in Inverse Emulsion Using Isohexadecane as Carrier Oil The procedure according to Example 1 was repeated, only replacing the 229.484 g of farnesane with 229.484 g of Isohexadecane.

Example 34 (Comparative): A sodium 2-acrylamido-2-methyl-1-propane sulfonate+sodium acrylate Copolymer Cross-Linked with methylene-bis-acrylamide in Inverse Emulsion Using Isopar M as Carrier Oil The procedure according to Example 3 was repeated, only replacing the 174.280 g of farnesane with 174.280 g of Isopar M.

Example 35 (Comparative): A sodium 2-acrylamido-2-methyl-1-propane sulfonate+sodium acrylate Copolymer Cross-Linked with methylene-bis-acrylamide in Inverse Emulsion Using Isohexadecane as Carrier Oil The procedure according to Example 3 was repeated, only replacing the 174.280 g of farnesane with 174.280 g of isohexadecane.

Example 36 (Comparative): A sodium 2-acrylamido-2-methyl-1-propane sulfonate Homocopolymer Cross-Linked with methylene-bis-acrylamide in Inverse Emulsion Using Isopar M as Carrier Oil The procedure according to Example 5 was repeated, only replacing the 229.484 g of farnesane with 229.484 g of Isopar M.

Example 37 (Comparative): A sodium 2-acrylamido-2-methyl-1-propane sulfonate Homocopolymer Cross-Linked with methylene-bis-acrylamide in Inverse Emulsion Using Isohexadecane as Carrier Oil The procedure according to Example 5 was repeated, only replacing the 229.484 g of farnesane with 229.484 g of isohexadecane.

Evaluation of Thickening Effectiveness in Acidic Media

Three different acid solutions were used to assess the thickening performance of the inverse emulsion copolymers under acidic conditions, these being 20% aqueous glycolic acid solution (pH=1.22), 20% aqueous phosphoric acid solution (pH=0.67), and 20% aqueous citric acid solution (pH=1.32).

In each test, the requisite amount of acid solution was weighed into a beaker, followed by the requisite amount of inverse emulsion copolymer. So, for example, to test the inverse emulsions at 5% level in citric acid, 190 g of the citric acid solution was weighed into the beaker followed by 10 g of inverse emulsion copolymer. The mixture was then stirred under high shear for 2 minutes using a stainless steel circular toothed blade powered by a variable speed electric stirrer motor before its viscosity was measured using a Brookfield, model DV-1 viscometer fitted with spindle 6 rotating at 5 rpm (glycolic acid and citric acid tests) or spindle 4 rotating at 5 rpm (phosphoric acid tests).

The results of these tests are set out in Tables XII to XIV. In each table, the numbers against each Example are viscosities measured in dPa·s Cross-linked sodium 2-acrylamido-2-methyl-1-propane sulfonate+Hydroxyethyl Methacrylate Copolymer Tests

TABLE XII

| | | ACID SOLUTION | | |
|---|---|---|---|---|
| | | Glycolic | Phosphoric | Citric |
| | | INVERSE EMULSION CONCENTRATION | | |
| | | 4.0% | 8.0% | 5.0% |
| Ex. 1 | (farnesane, inventive) | 354 | 366 | 520 |
| Ex. 32 | (Isopar M, comparative) | 248 | 69.6 | 320 |
| Ex. 33 | (isohexadecane, comparative) | 228 | 301 | 408 |

Cross-linked sodium 2-acrylamido-2-methyl-1-propane sulfonate+Sodium Acrylate Copolymer Tests

TABLE XIII

| | | ACID SOLUTION | | |
|---|---|---|---|---|
| | | Glycolic | Phosphoric | Citric |
| | | INVERSE EMULSION CONCENTRATION | | |
| | | 4.0% | 8.0% | 5.0% |
| Ex. 3 | (farnesane, inventive) | 81 | 314 | 116 |
| Ex. 34 | (Isopar M, comparative) | 44 | 0 | 78 |
| Ex. 35 | (isohexadecane, comparative) | 30 | 240 | 108 |

Cross-linked sodium 2-acrylamido-2-methyl-1-propane sulfonate Homopolymer Tests

TABLE XIV

| | | ACID SOLUTION | | |
|---|---|---|---|---|
| | | Glycolic | Phosphoric | Citric |
| | | INVERSE EMULSION CONCENTRATION | | |
| | | 4.0% | 8.0% | 5.0% |
| Ex. 5 | (farnesane, inventive) | 327 | 1460 | 410 |
| Ex. 36 | (Isopar M, comparative) | 20 | 0 | 12 |

TABLE XIV-continued

| | | ACID SOLUTION | | |
|---|---|---|---|---|
| | | Glycolic | Phosphoric | Citric |
| | | INVERSE EMULSION CONCENTRATION | | |
| | | 4.0% | 8.0% | 5.0% |
| Ex. 37 | (isohexadecane, comparative) | 170 | 182 | 396 |

These three Tables show that, for each copolymer, those inverse emulsions employing farnesane as carrier oil surprisingly produce higher viscosities in these acidic solutions than those employing the carrier oils Isopar M or isohexadecane, which were generally adopted as carrier oils for inverse emulsion copolymer thickeners in prior art formulations, as discussed herein.

The invention claimed is:

1. An inverse emulsion copolymer composition comprising
   (A) an aqueous phase comprising a cross-linked hydrophilic polyelectrolyte copolymer (A') obtained by the free radical copolymerisation of:
      (i) at least one anionic ethylenically unsaturated monomer bearing a negatively charged group and one polymerisable C=C double bond, or at least one cationic ethylenically unsaturated monomer bearing a positively charged group and one polymerisable C=C double bond, and
      (ii) at least one non-ionic ethylenically unsaturated cross-linking monomer bearing at least two polymerisable C=C double bonds, and
      (iii) optionally, one or more hydrophilic non-ionic ethylenically unsaturated monomers bearing one polymerisable C=C double bond,
   (B) an oil phase comprising a carrier oil (C), and
   (D)(i) at least one water-in-oil emulsifying surfactant, and
       (ii) at least one oil-in-water emulsifying surfactant;
   characterised in that the carrier oil component (C) comprises from 75% to 100%, by weight of the said carrier oil component (C), of farnesane.

2. An inverse emulsion copolymer composition according to claim 1, characterised in that the composition comprises from 10 to 40% by weight of carrier oil, based on the total of (A)+(B)+(D).

3. An inverse emulsion copolymer composition according to claim 1, characterised in that the carrier oil component (C) of the oil phase comprises from 90% to 100%, by weight of the said carrier oil component (C), of farnesane.

4. An inverse emulsion copolymer composition according to claim 1, characterised in that the carrier oil component (C) of the oil phases comprises an additional carrier oil component (C') which is one or more species selected from soyabean oil methyl or ethyl ester, linseed oil methyl or ethyl ester, coconut oil methyl or ethyl ester, castor oil methyl or ethyl ester, cottonseed oil methyl or ethyl ester, olive oil methyl or ethyl ester, rapeseed oil methyl or ethyl ester, methyl palmitate, methyl stearate, methyl linoleate, squalane, isosqualane, neosqualane, farnesane dimer, hexahydrofarnesene, tetrahydrofarnesene, dihydrofarnesene, or D-limonene.

5. An inverse emulsion copolymer composition according to claim 3, characterised in that 100% of the carrier oil component (C) of the oil phase consists of farnesane.

6. An inverse emulsion copolymer composition according to claim 1, characterised in that the ionic monomer component (A)(i) of the aqueous phase (A) is an anionic monomer.

7. An inverse emulsion copolymer composition according to claim 6, characterised in that the anionic monomer is an acid functional monomer selected from carboxylic acid functional monomers, sulphonic acid functional monomers, phosphoric acid functional monomers and phosphonic acid functional monomers.

8. An inverse emulsion copolymer composition according to either claim 7, characterised in that at least some of the acid functional monomer is neutralised with a base to convert at least some of the said acid functional monomer into its salt form.

9. An inverse emulsion copolymer composition according to claim 7, characterised in that the acid functional monomer is wholly neutralised with base to convert it into its salt form.

10. An inverse emulsion copolymer composition according to claim 8, characterised in that the base is selected from sodium hydroxide, potassium hydroxide or ammonium hydroxide.

11. An inverse emulsion copolymer composition according to claim 1, characterised in that the ionic monomer component (A)(i) of the aqueous phase (A) is a cationic monomer.

12. An inverse emulsion copolymer composition according to claim 11, characterised in that the cationic monomer is selected from N,N,N-trimethyl-3-[(2-methyl-1-oxo-2-propenyl) amino]-propanammonium chloride, N,N,N-trimethyl-3-[(1-oxo-2-propenyl)amino]-propanammonium chloride, [2-(methacryloyloxy)ethyl]trimethylammonium chloride, [2-(acryloyloxy)ethyl]trimethylammonium chloride, and [2-(methacryloyloxy)ethyl] dimethylbenzylammonium chloride.

13. An inverse emulsion copolymer composition according to claim 1, characterised in that the cross-linking monomer component (A)(ii) of the aqueous phase (A) is selected from allyl functional monomers and (meth)acrylate functional monomers.

14. An inverse emulsion copolymer composition according to claim 13, characterised in that the cross-linking monomer component (A)(ii) of the aqueous phase (A) is selected from triallylamine, triallyl cyanurate, ethoxylated trimethylolpropane tri(meth)acrylate and methylene-bis-acrylamide.

15. An inverse emulsion copolymer composition according to claim 1, characterised in that the optional hydrophilic, non-ionic monomer component (A)(iii) of the aqueous phase (A) is either absent or is selected from acrylamide and its derivatives and alkyl (meth)acrylate esters bearing one or more hydroxyl substituents on the alkyl group.

16. An inverse emulsion copolymer composition according to claim 15, characterised in that the optional hydrophilic, non-ionic monomer component (A)(iii) of the aqueous phase (A) is either absent or is selected from acrylamide, methacrylamide, N-methylacrylamide, 2-hydroxyethyl acrylate and hydroxyethyl methacrylate.

17. An inverse emulsion copolymer composition according to claim 1, characterised in that the composition comprises from 10% to 50% by weight of cross-linked hydrophilic polyelectrolyte copolymer (A'), based on the total of (A)+(B)+(D).

18. An inverse emulsion copolymer composition according to claim 1, characterised in that the cross-linked hydrophilic polyelectrolyte copolymer (A') is obtained by the free radical copolymerisation of either:
  a) Sodium 2-acrylamido-2-methyl-propane sulfonate, hydroxyethyl methacrylate and methylene-bis-acrylamide; or
  b) Sodium 2-acrylamido-2-methyl-propane sulfonate, sodium acrylate and methylene-bis-acrylamide; or
  c) Sodium 2-acrylamido-2-methyl-propane sulfonate and methylene-bis-acrylamide; or
  d) [2-(Acryloyloxy)ethyl]trimethylammonium chloride and methylene-bis-acrylamide.

19. A process for preparing an inverse emulsion copolymer composition as claimed in claim 1, which process comprises forming a water-in-oil emulsion of a monomer composition which contains monomers (A)(i), (A)(ii) and, optionally, (A)(iii), and subjecting the monomer composition to inverse emulsion polymerisation in the presence of carrier oil component (C) and surfactant (D)(i) to form a cross-linked hydrophilic polyelectrolyte copolymer (A'), characterised in that 75% to 100% of the carrier oil component comprises farnesane; and adding a surfactant D(ii) to provide the inverse emulsion copolymer composition.

20. A process according to claim 19, which comprises:
  dissolving monomers (A)(i), (A)(ii) and, optionally, (A)(iii) in aqueous solution;
  combining the aqueous solution with carrier oil component (C) and surfactant (D)(i) to form a water-in-oil emulsion;
  performing free radical polymerisation to form a cross-linked hydrophilic polyelectrolyte copolymer (A') in the inverse emulsion; and
  adding a surfactant (D)(ii) to provide an inverse emulsion copolymer thickener.

* * * * *